(12) United States Patent
Low et al.

(10) Patent No.: US 11,712,493 B2
(45) Date of Patent: Aug. 1, 2023

(54) APPARATUS AND METHOD FOR AIR FRESHENING

(71) Applicant: The Procter & Gamble Company, Cincinnati, OH (US)

(72) Inventors: Bee Ting Low, Singapore (SG); Qunhui Guo, Pittsburgh, PA (US); Luciano M. Parrinello, Pittsburgh, PA (US)

(73) Assignee: The Procter & Gamble Company, Cincinnati, OH (US)

( * ) Notice: Subject to any disclaimer, the term of this patent is extended or adjusted under 35 U.S.C. 154(b) by 683 days.

(21) Appl. No.: 16/795,612

(22) Filed: Feb. 20, 2020

(65) Prior Publication Data

US 2020/0276352 A1   Sep. 3, 2020

Related U.S. Application Data

(60) Provisional application No. 62/811,541, filed on Feb. 28, 2019.

(51) Int. Cl.
*A61L 9/12* (2006.01)
*A61L 9/01* (2006.01)
*B60H 3/00* (2006.01)

(52) U.S. Cl.
CPC ............. *A61L 9/12* (2013.01); *B60H 3/0028* (2013.01); *A61L 9/01* (2013.01); *A61L 2209/131* (2013.01); *A61L 2209/21* (2013.01)

(58) Field of Classification Search
CPC ........ A61L 2209/13; A61L 9/00; A61L 9/012; A61L 9/04; A61L 9/042; A61L 9/044; A61L 2101/32; B61H 3/0028
(Continued)

(56) References Cited

U.S. PATENT DOCUMENTS 2,940,830 A   6/1960   Thornhill
4,681,750 A   7/1987   Johnson et al.
(Continued)

FOREIGN PATENT DOCUMENTS

JP         2014015523 A    1/2014
WO    WO2010121039 A2   10/2010
WO    WO2011129928 A1   10/2011

*Primary Examiner* — Monzer R Chorbaji
(74) *Attorney, Agent, or Firm* — Carolyn S. Powell; George H. Leal; Abbey A. Lopez

(57) ABSTRACT

An apparatus for air freshening in an interior occupancy space. The apparatus has a reservoir containing a volatile composition for air freshening and/or malodor removal and a composite membrane in fluid communication with the volatile composition. The composite membrane has a first side facing the reservoir and a second side opposite the first side. At least one of the first side and the second side has a diffusion regulating coating, the diffusion regulating coating including a hydrophobic/oleophobic material having at least one fluoro-alkyl group. The volatile composition includes at least 20% of perfume raw materials by weight of the composition, the at least 20% of perfume raw materials having an average vapor pressure equal to or greater than 0.01 torr at 25 degrees Celsius. The apparatus has an average vapor release rate from 0.2 mg/hr*cm$^2$ to 5 mg/hr*cm$^2$ at an air flow rate of 5 m/s and a temperature of 21 degrees Celsius.

16 Claims, 5 Drawing Sheets

(58) Field of Classification Search
USPC .................................... 422/1, 5, 306; 239/6
See application file for complete search history.

(56) References Cited

U.S. PATENT DOCUMENTS

| | | | |
|---|---|---|---|
| 6,013,732 | A | 1/2000 | Tamana et al. |
| 7,498,369 | B2 | 3/2009 | Whear et al. |
| 8,551,895 | B2 | 10/2013 | Yahiaoui et al. |
| 9,149,552 | B1 | 10/2015 | Do |
| 2007/0176015 | A1 | 8/2007 | Farrell et al. |
| 2010/0314461 | A1* | 12/2010 | Gruenbacher ....... B60H 3/0028 239/6 |
| 2017/0000102 | A1 | 1/2017 | Parrinello |
| 2019/0070330 | A1 | 3/2019 | Parrinello et al. |

\* cited by examiner

APPARATUS AND METHOD FOR AIR FRESHENING

CROSS-REFERENCE

This application claims the benefit of provisional Application No. 62/811,541, filed Feb. 28, 2019.

FIELD OF THE INVENTION

The present invention relates to an apparatus and a method for air freshening in an interior occupancy space.

BACKGROUND OF THE INVENTION

Devices for dispensing volatile materials are well known and commonly used to deliver a variety of benefits such as freshening, malodor removal or scenting of air in spaces in household and commercial establishments such as rooms, or enclosed spaces such as a vehicle passenger compartment space. For example, air freshening products have been designed for dispensing volatile materials such as a volatile composition comprising one or more volatile materials like perfume oils. The volatile composition may be contained in, for example, a spray bottle and be sprayed into the air of interior spaces as droplets which transition to vapor. However, such products do not continuously freshen (i.e., the volatile composition is only dispensed upon manual activation). Alternatively, volatile compositions may be dispensed through systems which do not require manual actuation such as via evaporating the volatile composition from membrane based, wick based and gel based systems.

However, a problem with such air freshening products is often an inconsistency in the evaporation rate of the volatile composition over the product life, i.e. high evaporation rate of the volatile composition at the beginning of product use and low evaporation rate towards end of product life. Specifically, the volatile composition typically comprises a mixture of highly volatile compounds and other volatile compounds which are less volatile ("less volatile compounds"). Highly volatile compounds generally have higher vapor pressures than the less volatile compounds. Specifically, at a given temperature, a highly volatile compound with a higher vapor pressure vaporizes more readily than a less volatile compound with a lower vapor pressure. In use, the highly volatile compounds tend to evaporate more quickly at the beginning of such a product's use, while the less volatile compounds evaporate later, resulting in an overall inconsistent scent intensity and fragrance character of the volatile composition over the product life. The high initial evaporation rate can result in an overpowering initial scent intensity which can create a perception that the air freshener product has a different scent intensity over the product life or that the product is no longer effective after the initial scent intensity is no longer present.

In particular, car vent air fresheners attachable to the car vent provide at least one advantage by quickly providing freshness throughout the car when air flow occurs through the vent and moves past the air freshener. However, it is also a challenge to prevent a "too strong scent intensity" during high air flow conditions such as during use of the air conditioning system or the heater of a heating, ventilation, and air conditioning (HVAC) system or during driving. Further, there is also a continuing need to provide users a "well balanced" scent character that generally include top, middle, and bottom scent "notes.". Therefore, there exists a need for an apparatus for delivering a volatile composition at a reduced evaporation rate and for controlled release of the volatile composition. There is also a need for an apparatus and method to provide a consistent evaporation rate, scent intensity and/scent character over time.

SUMMARY OF THE INVENTION

The present invention relates to an apparatus for air freshening in an interior occupancy space, the apparatus comprising:
 a) a reservoir containing a volatile composition for air freshening and/or malodor removal;
 b) a composite membrane in fluid communication with the volatile composition; wherein the composite membrane comprises a first side facing the reservoir and a second side opposite the first side;
 c) wherein at least one of the first side and the second side comprises a diffusion regulating coating, wherein the diffusion regulating coating comprises a hydrophobic/oleophobic material comprising at least one fluoro-alkyl group;
 d) wherein the volatile composition comprises at least 20% of perfume raw materials by weight of the composition, wherein the at least 20% of perfume raw materials have an average vapor pressure equal to or greater than 0.01 torr at 25 degrees Celsius;
 e) wherein the apparatus comprises an average vapor release rate from 0.2 mg/hr*cm$^2$ to 5 mg/hr*cm$^2$ at an air flow rate of 5 m/s+/−1 m/s and a temperature of 21 degrees Celsius.

DETAILED DESCRIPTION OF THE INVENTION

Figure 1:
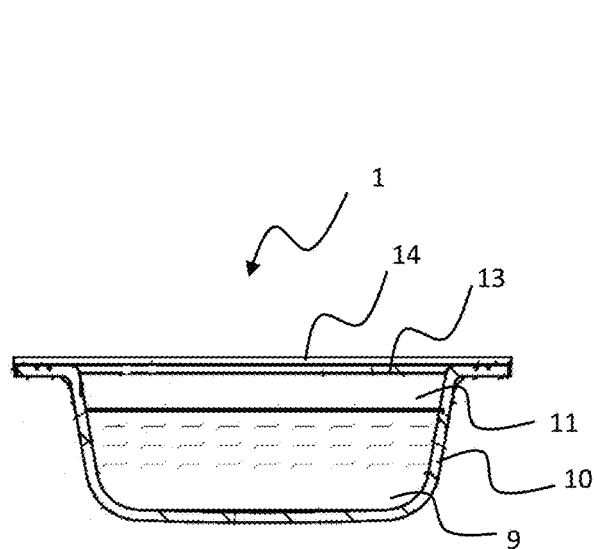
FIG. 1 is a side section view of an apparatus for controlled release of a volatile composition according to the present invention.

The present invention relates to an apparatus and a method for air freshening in an interior occupancy space in a continuous manner. Specifically, the apparatus comprises a reservoir for containing a liquid phase or a solid phase of a volatile composition. The volatile composition comprises a mixture of perfume raw materials which can evaporate at or near room temperature and atmospheric pressure without the need for an external energy source. It has also been surprisingly found that providing a composite membrane with a diffusion regulating coating in the apparatus having the volatile composition at an air vent of an air conditioning system enables controlled release of the volatile composition from the apparatus when the air conditioning system is turned on thereby enabling a reduced average vapor release rate of the volatile composition and reducing the scent intensity of the volatile composition in the interior occupancy space.

A technical effect of a volatile composition having the mixture of perfume raw materials and the composite membrane having a diffusion regulating coating is the vapor release rate of the apparatus in combination with the volatile composition can be measurably reduced while using the apparatus on the vent in an interior space such as in an automobile thereby reducing scent intensity rather than relying on adjusting air flow openings in an air freshener.

In the following description, the apparatus described is a consumer product, such as a car air freshener, for evaporating a volatile composition in an interior occupancy space of an automobile to deliver a variety of benefits such as freshening, malodor removal or scenting of air in an interior occupancy space such as a vehicle passenger compartment space. However, it is contemplated that the apparatus may be configured for use in a variety of applications to deliver a volatile composition to provide the benefits in interior occupancy spaces such as rooms in household and commercial establishments with air conditioning systems, and the apparatus may include but is not limited to consumer products, such as, for example air freshening products, air fresheners or the like.

For the purposes of illustrating the present invention in detail, the invention is described below as a non-energized apparatus having a membrane in fluid communication with the volatile composition. However, it will be appreciated that the apparatus of the present invention can be energized or non-energized. Prior to describing the present invention in detail, the following terms are defined for clarity. Terms not defined should be given their ordinary meaning as understood by a skilled person in the relevant art.

"Hydrophilic" as used herein, means that a side of the membrane over which a hydrophilic coating is applied demonstrates a water contact angle of less than 90° using the Kruss Drop Shape Analysis.

"Hydrophobic" as used herein, means that a side of the membrane over which a hydrophobic material is applied demonstrates a water contact angle of at least 90° using the Kruss Drop Shape Analysis.

"Oleophobic" as used herein, means that a side of the membrane over which a hydrophobic/oleophobic material is applied demonstrates an oil rating of at least 6, such as at least 7 or at least 8, based on AATCC test method 118-2007.

"Horizontal orientation" as used herein, refers to a position of an apparatus according to the present invention wherein the membrane is facing the environment in an upward or downward position.

"interior occupancy space" refers to a finite volume of space in a residential, commercial or vehicle environment.

"Membrane" as used herein, refers to a semi-permeable material which allows some components of matter to pass through but stops other components. Of the components that pass through, the membrane moderates the permeation of components i.e. some components permeate faster than other components. Such components may include molecules, ions or particles.

"Microporous membrane" as used herein, refers to a material having a network of pores.

"Composite membrane" as used herein, refers to a membrane having two or more different materials. The composite membrane may include a substrate having the two or more different materials applied to the substrate to form the composite membrane.

"Non-energized" means that the apparatus is passive and does not require to be powered by a source of external energy. In particular, the apparatus does not need to be powered by a source of heat, gas or electrical current. The apparatus may also be configured as an energized device. An exemplary energized device may be an electrical device. The energy source of the energized device may be an electrical car outlet or battery-operated air freshener having a membrane as described in the following description to transport a volatile composition and/or evaporate a volatile composition therefrom; or other heating devices (e.g. devices powered by chemical reactions such as catalyst fuel systems; solar powered devices, etc.).

"Touchpoint" as used herein, refers to a point of contact or interaction between the use of an air freshener (or apparatus) and a consumer of the volatile composition.

"Vertical orientation" as used herein, refers to a position of an apparatus according to the present invention wherein the membrane is facing the environment in a forward facing position or in a rear facing position.

"Volatile composition" as used herein, refers to a material that is vaporizable at room temperature and atmospheric pressure without the need of an additional energy source. The volatile composition may be configured for various uses such as air freshening, deodorization, odor elimination, malodor counteraction, mood enhancement, aromatherapy aid, scented compositions, non-scented compositions. Further, it is not necessary for all of the component materials of the volatile composition to be volatile. Any suitable volatile composition in any amount or form, including a liquid, solid, gel or emulsion, may be used. Materials suitable for use herein may include non-volatile compounds, such as carrier materials (e.g., water, solvents, etc.). It should also be understood that when the volatile composition is described herein as being "delivered", "emitted", or "released", this refers to the volatization of the volatile component thereof and does not require that the non-volatile components thereof be emitted.

FIG. 1 is a side section view of an apparatus 1 according to the present invention in a horizontal orientation when the apparatus 1 is placed on a support. The apparatus 1 can be constructed as a disposable, single-use item or one that it is replenished with a volatile composition. The apparatus 1 comprises a container 10 containing a reservoir 11 having a volatile composition 9. The container 10 may be made of a substantially vapor impermeable material designed to resist diffusion of a vapor phase of the volatile composition 9. For example, the container 10 may be made of metal, glass, ceramic, porcelain, tile and plastic including but not limited to thermoplastics and other known materials suitable for thermoforming, injection molding and blow molding. A composite membrane 13 may be disposed within the container 10 and arranged to be in fluid communication with the volatile composition 9. The apparatus 1 may further include a vapor impermeable substrate 14 adjacent to the membrane 13 wherein the vapor impermeable substrate 14 is configured to prevent release of the volatile composition 9 before use. Specifically, the apparatus 1 comprises an average vapor release rate from 0.2 mg/hr*cm$^2$ to 5 mg/hr*cm$^2$ at an air flow rate of 5 m/s and a temperature of 21 degrees Celsius which corresponds to a consumer perceived sensory feeling of a scent intensity that is not overwhelming, i.e. "just nice" scent intensity.

Composite Membrane

Figure 2:
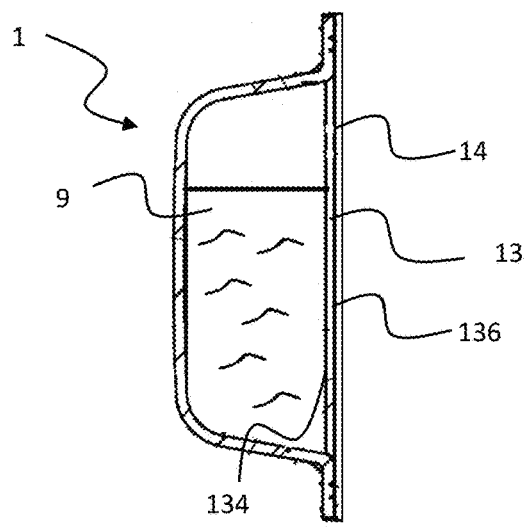
FIG. 2 is a side section view of the apparatus shown in FIG. 1 in a vertical orientation when the apparatus is placed on a support.

The composite membrane 13 includes a layer of porous material that is vapor permeable and is designed to be capable of wicking liquid, yet prevents free flow of liquid out of the composite membrane 13. Referring to FIG. 2, the composite membrane 13 may comprise a first side 134 facing the reservoir 11 and a second side 136 opposite the first side 134, wherein the second side 136 faces the atmosphere and away from the reservoir 11. The first and second sides 134, 136 may be comprised in a substrate 12 such as for example a microporous membrane 12 that is uncoated (hereinafter "membrane"). The membrane 12 includes a thermoplastic organic polymer including a polyolefin. The membrane 12 defines a network of interconnecting pores communicating substantially throughout the microporous membrane 12. Finely divided, particulate filler may be distributed throughout the membrane 12. Subsequent materials may be applied to the membrane 12 to form a diffusion regulating coating 138 on at least one of the first side 134 and the second side 136 of the membrane 12. In some examples, only the first side 134 of the membrane 12 receives the materials. In some examples, only the second side 136 of the membrane 12 receives the materials. In some examples, both the first side 134 and the second side 136 of the membrane 12 receive the materials. The diffusion regulating coating 138 may comprise a coating weight of 0.01 to 5.5 g/m$^2$, from 0.05 to 2.0 g/m$^2$, from 0.05 to 0.5 g/m$^2$ or different combinations of the upper and lower percentages described above or combinations of any integer in the ranges listed above.

Figure 3A:
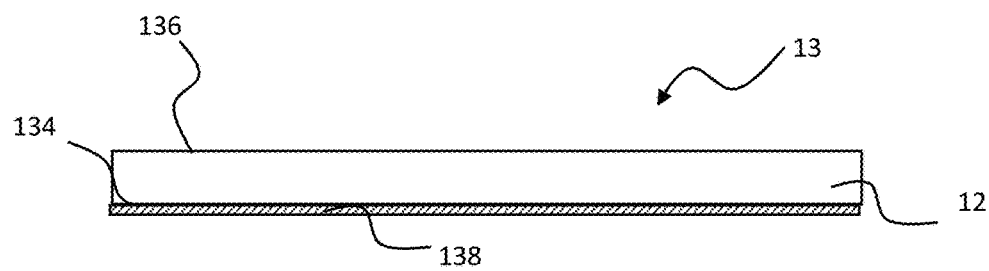
FIGS. 3A to 3C are side schematic views of different arrangements of a diffusion regulating coating on a composite membrane for an apparatus according to the present invention.
Figure 3B:
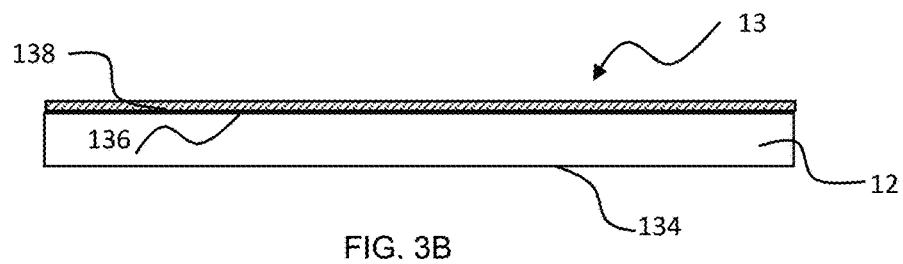
Figure 3C:
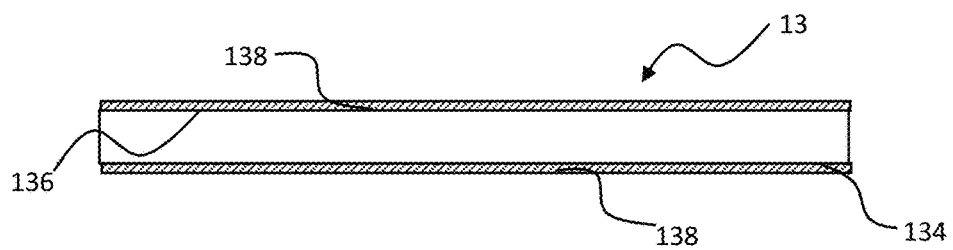

Referring to FIGS. 3A to 3C, the diffusion regulating coating 138 may cover at least a portion of at least one of the first side 134 and the second side 136. The diffusion regulating coating 138 may be applied to the first side 134 of the membrane 12 (as shown in FIG. 3A), on the second side 136 of the membrane 12 (as shown in FIG. 3B) or on both first and second sides 134, 136 of the membrane 12 (as shown in FIG. 3C).

At least a part of the diffusion regulating coating 138 comprises a hydrophobic/oleophobic material 2C comprising at least one fluoro-alkyl group. Without wishing to be bound by theory, a technical effect of providing a hydrophobic/oleophobic material 2C is this results in an overall reduced vapor release rate in the apparatus 1 when the apparatus 1 is placed on an air vent.

Figure 4A:
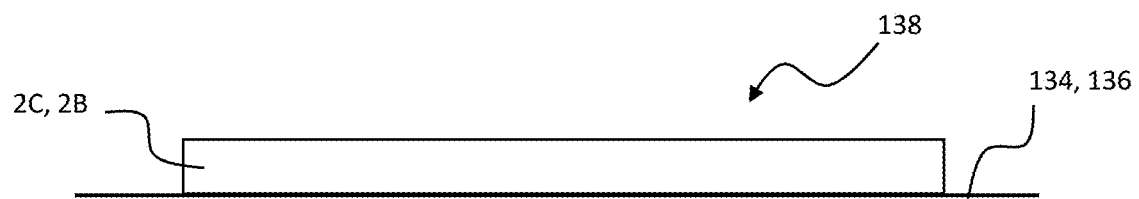
FIGS. 4A to 4C are side schematic views of different structure configurations of materials for a diffusion regulating coating on a composition membrane for an apparatus according to the present invention.

In an exemplary embodiment, the diffusion regulating coating 138 may further comprise a polymer material 2. Referring to FIG. 4C, the polymer material may be disposed over at least a portion of the at least one of the first side 134 and the second side 136. Referring to FIG. 4C, the hydrophobic/oleophobic material 2C is on the polymer material 2 defining the diffusion regulating coating 138.

The polymer material 2 may be a hydrophilic material or a hydrophobic material. The polymer material 2 may be a hydrophobic material comprises one or more of a polysiloxane, polydimethylsiloxane, polyvinylidene fluoride, polyacrylonitrile and combinations thereof.

In an exemplary embodiment, the polymer material 2 is a hydrophilic material, preferably a hydrophilic coating layer 2B as described hereinafter.

A. First Hydrophobic/Oleophobic Material

The hydrophobic/oleophobic material 2C may be a first hydrophobic/oleophobic material 2C may be applied to the membrane 12 to define the diffusion regulating coating 138. FIG. 4A shows a cross section schematic view of the diffusion regulating coating 138 comprising the first hydrophobic/oleophobic material 2C. The first hydrophobic/oleophobic material 2C may be hydrophobic. The side of the membrane 12 over which the first hydrophobic/oleophobic material 2C is applied may demonstrate a water contact angle of at least 105°, such as at least 110°, at least 115°, at least 120°, at least 125°, at least 130°, at least 135°, at least 140°, or at least 150°. The first hydrophobic/oleophobic material 2C may be oleophobic. Oleophobic means that the side of the membrane 12 over which the first hydrophobic/oleophobic material 18 is applied demonstrates an oil rating of at least 6, such as at least 7 or at least 8, based on AATCC test method 118-2007.

The first hydrophobic/oleophobic material 2C may be hydrophobic and oleophobic. In some examples, the first hydrophobic/oleophobic material 2C may form a coating over the membrane 12. In other examples, the first hydrophobic/oleophobic material 2C may not form a coating over the membrane 12 but may instead be a surface treatment to the membrane 12. Surface treatment, in this situation, means that the first hydrophobic/oleophobic material 2C chemically reacts with the membrane 12 (such as the siliceous filler dispersed throughout the membrane 12) so as to form a hydrophobic/oleophobic region of the membrane 12.

The first first hydrophobic/oleophobic material 2C may include at least one fluoro-alkyl group and/or include a polymer including at least one fluoro-alkyl group. The first hydrophobic/oleophobic material 2C may be a fluoro-alkyl group containing co-polymer. An exemplary hydrophobic/oleophobic material 2C comprises one or more of a fluoroalkyl acrylate copolymer, perfluoroalkoxy polymer, polytetrafluoroethylene, fluorinated ethylene-propylene, polyethylenetetrafluoroethylene, perfluoro elastomers, perfluoropolyether, fluorosilicones, fluorosilanes, perfluorosilane and fluoroalkylsilsequioxane.

Further, the first hydrophobic/oleophobic material 2C may be a polyacrylate co-polymer having a fluorinated polymer. In one non-limiting example, the first hydrophobic/oleophobic material 2C may include products sold under the Unidyne tradename, available from Daikin Industries, Ltd. (Osaka, Japan). The first hydrophobic/oleophobic material 2C may include any of the fluoro-alkyl group containing polymers or co-polymers described in U.S. Pat. No. 6,013,732 or 8,551,895, which are incorporated herein in their entireties by reference. The first hydrophobic/oleophobic material 2C may include a polymer including some fluorination in the side chains or ends of the polymer, with the backbone of the polymer being substantially free of fluorine groups (distinguishable from perfluorinated polymers).

The first hydrophobic/oleophobic material 2C may include an alkoxysilane compound having at least one fluoro-alkyl group. The first hydrophobic/oleophobic material 2C including the alkoxysilane compound having at least one fluoro-alkyl group may interact with the membrane 12 (such as with the siliceous filler) through a condensation reaction with filler and may form a hydrophobic/oleophobic region of the membrane 12. Non-limiting examples of the alkoxysilane compound having at least one fluoro-alkyl group are (tridecafluoro-1,1,2,2-tetrahydrooctyl)triethoxysilane (see Formula I below) or (tridecafluoro-1,1,2,2 tetrahydrooctyl)trimethoxysilane.

Formula I

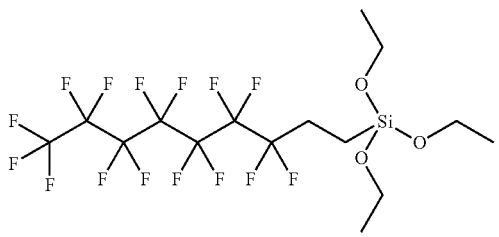

As shown in FIG. 4A, the first hydrophobic/oleophobic material 2C may e applied over the first side 134 of the membrane 12 without any material applied over the second side 136 to define a diffusion regulating coating 138. Alternatively, the first hydrophobic/oleophobic material 2C may be applied over the second side 136 of the membrane 12 without any material applied over the first side 134 to define a diffusion regulating coating 138. Alternatively, the first hydrophobic/oleophobic material 2C may be applied over the first side 134 of the membrane 12 to define a first diffusion regulating coating 138 with a second material also being applied on the second side 136 (see FIG. 3C) to define a second diffusion regulating coating 138.

In exemplary examples, additional material may be applied over top of or underneath the first hydrophobic/oleophobic material 2C. A hydrophobic/oleophobic material (s), a hydrophilic coating layer(s), a hydrophobic material or some combination thereof may be applied to the membrane 12.

Figure 4B:
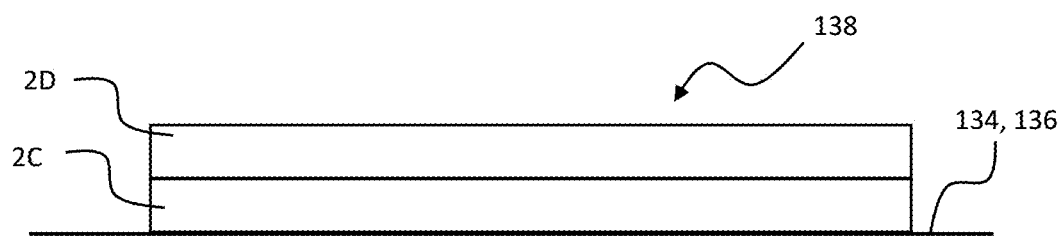
Figure 4C:
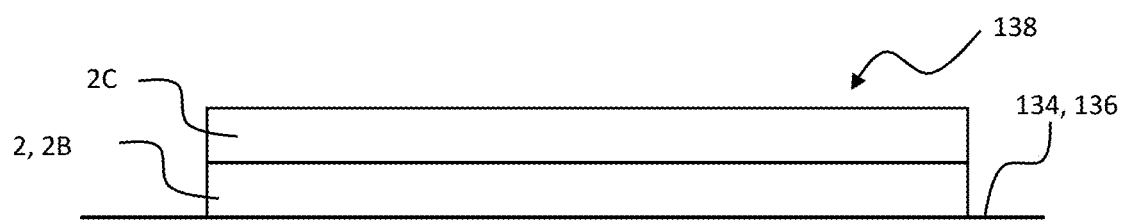

Referring to FIG. 4B, the first hydrophobic/oleophobic material 2C is in direct contact with the first side 134 and/or the second side 136 of the membrane 12. The first hydrophobic/oleophobic material 2C may be applied to the first side 134 and/or the second side 136 of the membrane 12 using any suitable method such as spray application, curtain coating, dip coating, slot die coating, screen printing, and/or drawn-down coating, e.g., by means of a doctor blade or draw-down bar, techniques.

B. Second Hydrophobic/Oleophobic Material

Referring to FIG. 4B, the membrane 12 may be coated with a second hydrophobic/oleophobic material 2D. The second hydrophobic/oleophobic material 2D may be applied to the first side 134 of the membrane 12 and/or the second side 136 of the membrane 12 to define a diffusion regulating coating 138 (as shown in FIGS. 3A to 3C). The second hydrophobic/oleophobic material 2D may be hydrophobic. The side (such as the first side 134 or the second side 136) of the membrane 12 over which the second hydrophobic/oleophobic material 2D is applied may demonstrate a water contact angle of at least 105°, such as at least 110°, at least 115°, at least 120°, at least 125°, at least 130°, at least 135°, at least 140°, or at least 150°. The second hydrophobic/oleophobic material 2D may be chosen from any of the materials of the previously described first hydrophobic/oleophobic material 2D.

Referring to FIG. 4B, the second hydrophobic/oleophobic material 2D may be applied over the second side 136 of the membrane 12 opposite the first side 134, which has the first hydrophobic/oleophobic material 2C applied thereon. The second hydrophobic/oleophobic material 2D on the second side 136 may be the same hydrophobic/oleophobic material or a different hydrophobic/oleophobic material from the first hydrophobic/oleophobic material 2C on the first side 134. Additional materials may be applied over top of or underneath the second hydrophobic/oleophobic material 2D. Alternatively, the second hydrophobic/oleophobic material 2D may be a separate coating in direct contact with the first side 134 and/or the second side 136 of the membrane 12.

The second hydrophobic/oleophobic material 2D may be applied to the first side 134 and/or the second side 136 of the membrane 12 using any suitable method such as spray application, curtain coating, dip coating, slot die coating, screen printing, and/or drawn-down coating, e.g., by means of a doctor blade or draw-down bar, techniques. In one non-limiting embodiment, the second hydrophobic/oleophobic material 2D is applied to the second side 136 of the membrane 12 using a draw-down method such that only the second side 136 of the membrane 12 is coated with second hydrophobic/oleophobic material 2D and not the first side 134.

C. Hydrophilic Coating Layer

Referring to FIG. 4A, the membrane 12 may be coated with at least one hydrophilic coating 2B. The hydrophilic coating 2B may be applied to the first side 134 of the membrane and/or the second side 136 of the membrane 12 (as shown in FIGS. 3A to 3C). The hydrophilic coating 2B may be hydrophilic. Hydrophilic means that the side of the membrane 12 over which the hydrophilic coating 2B is applied demonstrates a water contact angle of less than 90° using the Kruss Drop Shape Analysis. The side of the membrane 12 over which the hydrophilic coating 2B is applied may demonstrate a water contact angle of less than 85°, such as less than 80°, less than 70°, less than 60°, less than 50°, less than 40°, less than 30°, less than 20°, or less than 10°. The hydrophilic coating 2B may include one or more of a polyoxazoline, triblock copolymers based on poly(ethylene glycol)-poly(propylene glycol)-poly(ethylene glycol), polyamide, oxidized polyethylene or its derivatives, polyethyleneoxide, polyvinylpyrrolidone, poly(meth)acrylic acid, polyethylene glycol or its derivatives, polypropylene oxide or its derivatives, a copolymer of poly(ethylene glycol) and polyethyleneoxide, polyvinyl alcohol, cellulose or its derivatives, collagen, polypeptides, guar, pectin, polyimide, poly(meth)acrylamide, polysaccharides, zwitterionic polymers, polyampholytes, and polyethylenimine.

As shown in FIG. 4C, the hydrophilic coating 2B may be applied over the second side 136 of the membrane 12 opposite the first side 134, and the first hydrophobic/oleophobic material 2C is applied thereover to define a diffusion regulating coating 138. Additional materials may be applied over top of or underneath the hydrophilic coating 2B. In some examples, the hydrophilic coating 2B is in direct contact with the first side 134 and/or the second side 136 of the membrane 12. Data demonstrating the reduced vapor release rate of inventive apparatus 1 according to the present invention is illustrated in the Examples described hereinafter with reference to FIGS. 8 to 11.

The hydrophilic coating 2B may be applied to the first side 134 and/or the second side 136 of the membrane 12 using any suitable method such as spray application, curtain coating, dip coating, slot die coating, screen printing, and/or drawn-down coating, e.g., by means of a doctor blade or draw-down bar, techniques.

In some examples, the membrane 12 may be pre-treated (before any other material is applied to the membrane 12, such as the first hydrophobic/oleophobic material 2C, the second hydrophobic/oleophobic material 2D, or other hydrophilic coating 2B. The pre-treatment may be applied as a coating to the membrane 12, and the pre-treatment may be a hydrophilic coating, as previously described. The pre-treatment may improve uniformity of the subsequently applied material(s), such as the hydrophobic/oleophobic materials or other hydrophilic coating(s). The hydrophilic pre-treatment may be applied to the membrane 12 using any suitable method. In one example, the membrane 12 is dipped into a bath including the hydrophilic pretreatment.

The hydrophilic pre-treatment may be applied using other art-related methods, such as spray application, curtain coating, slot die coating, screen printing, and/or drawn-down coating, e.g., by means of a doctor blade or draw-down bar, techniques. The hydrophilic pretreatment may be applied to the first side 134, the second side 136, or the entire membrane 12. After the hydrophilic pre-treatment is applied, the pre-treated membrane 12 may be dried prior to any application of subsequent materials.

Further, certain characteristics of the composite membrane 13 may be altered by dispersing one or more fillers within the membrane 12. Fillers can adjust the physical properties of the composite membrane 13, such as strength, stiffness, and other tensile properties. There are many known filler and plasticizer materials, including, but not limited to, silica, clays, zeolites, carbonates, charcoals, and mixtures thereof. An example of a filled membrane 12 is an ultra-high molecular weight polyethylene (UHMWPE) membrane filled with silica, such as those described in U.S. Pat. No. 7,498,369. Although any suitable fill material and weight percentage may be used, typical fill percentages for silica, may be between about 50% to about 80%, about 60% to about 80%, about 70% to about 80%, or about 70% to about 75% of the total weight of the membrane. Examples of suitable membrane thicknesses include, but are not limited to between about 0.01 mm to about 1 mm, between about 0.1 mm to 0.4 mm, about 0.15 mm to about 0.35 mm, or about 0.25 mm. An exemplary microporous membrane 12 for the composite membrane 13 is described below.

Microporous Membrane

The microporous membrane 12 may include a thermoplastic organic polymer. In some examples, the thermoplastic organic polymer may be a substantially water-insoluble thermoplastic organic polymer. Substantially water-insoluble means having <50 mg/L solubility in pure water at 25° C.

The types of polymers suitable for use in the membrane 12 are numerous. In general, any substantially water-insoluble thermoplastic organic polymer which can be extruded, calendered, pressed, or rolled into film, sheet, strip, or web may be used. The polymer may be a single polymer or it may be a mixture of polymers. The polymers may be homopolymers, copolymers, random copolymers, block copolymers, graft copolymers, atactic polymers, isotactic polymers, syndiotactic polymers, linear polymers, or branched polymers. When mixtures of polymers are used, the mixture may be homogeneous or it may comprise two or more polymeric phases.

An example of suitable substantially water-insoluble thermoplastic organic polymers includes thermoplastic polyolefins. The polyolefins may comprise at least 2 weight percent, such as at least 5 weight percent, at least 10 weight percent, at least least 15 weight percent, at least 25 weight percent, at least 35 weight percent, at least 45 weight percent, at least 55 weight percent, at least 65 weight percent, at least 75 weight percent, or at least 85 weight percent of the membrane 12, based on the total weight of the membrane 12 including particulate filler. The polyolefins may comprise up to 95 weight percent, such as up to 85 weight percent, up to 75 weight percent, up to 65 weight percent, up to 55 weight percent, up to 45 weight percent, up to 35 weight percent, up to 25 weight percent, or up to 15 weight percent of the membrane 12, based on the total weight of the membrane 12 including particulate filler. The polyolefin may comprise 2 to 95 weight percent of the membrane 12, based on the total weight of the membrane 12 including particulate filler. Other examples of classes of suitable substantially water-insoluble organic polymers may include poly(halo-substituted olefins), polyesters, polyamides, polyurethanes, polyureas, poly(vinyl halides), poly(vinylidene halides), polystyrenes, poly(vinyl esters), polycarbonates, polyethers, polysulfides, polyimides, polysilanes, polysiloxanes, polycaprolactones, polyacrylates, and polymethacrylates. Contemplated hybrid classes, from which the substantially water-insoluble thermoplastic organic polymers may be selected include, for example, thermoplastic poly(urethane-ureas), poly(ester-amides), poly(silane-siloxanes), and poly(ether-esters). Further examples of suitable substantially water-insoluble thermoplastic organic polymers may include thermoplastic high density polyethylene, low density polyethylene, ultrahigh molecular weight polyethylene, polypropylene (atactic, isotactic, or syndiotactic), poly(vinyl chloride), polytetrafluoroethylene, copolymers of ethylene and acrylic acid, copolymers of ethylene and methacrylic acid, poly(vinylidene chloride), copolymers of vinylidene chloride and vinyl acetate, copolymers of vinylidene chloride and vinyl chloride, copolymers of ethylene and propylene, copolymers of ethylene and butene, poly(vinyl acetate), polystyrene, poly(omegaaminoundecanoic acid), poly(hexamethylene adipamide), poly(epsilon-caprolactam), and poly(methyl methacrylate). The recitation of these classes and example of substantially waterinsoluble thermoplastic organic polymers is not exhaustive, and are provided only for purposes of illustration.

Substantially water-insoluble thermoplastic organic polymers may in particular include, for example, poly(vinyl chloride), copolymers of vinyl chloride, or mixtures thereof. In an embodiment, the water-insoluble thermoplastic organic polymer includes an ultrahigh molecular weight polyolefin selected from: ultrahigh molecular weight polyolefin, e.g., essentially linear ultrahigh molecular weight polyolefin) having an intrinsic viscosity of at least 10 deciliters/gram; or ultrahigh molecular weight polypropylene, e.g., essentially linear ultrahigh molecular weight polypropylene) having an intrinsic viscosity of at least 6 deciliters/gram; or mixtures thereof. In a particular embodiment, the water-insoluble thermoplastic organic polymer includes ultrahigh molecular weight polyethylene, e.g., linear ultrahigh molecular weight polyethylene, having an intrinsic viscosity of at least 18 deciliters/gram.

Ultrahigh molecular weight polyethylene (UHMWPE) is not a thermoset polymer having an infinite molecular weight, but is technically classified as a thermoplastic. However, because the molecules are substantially very long chains, UHMWPE softens when heated but does not flow as a molten liquid in a normal thermoplastic manner. The very long chains and the peculiar properties they provide to UHMWPE may contribute in large measure to the desirable properties of the membrane 12 made using this polymer.

As indicated earlier, the intrinsic viscosity of the UHMWPE is at least about 10 deciliters/gram. Usually the intrinsic viscosity is at least about 14 deciliters/gram. Often the intrinsic viscosity is at least about 18 deciliters/gram. In many cases the intrinsic viscosity is at least about 19 deciliters/gram. Although there is no particular restriction on the upper limit of the intrinsic viscosity, the intrinsic viscosity is frequently in the range of from about 10 to about 39 deciliters/gram, e.g., in the range of from about 14 to about 39 deciliters/gram. In some cases the intrinsic viscosity of the UHMWPE is in the range of from about 18 to about 39 deciliters/gram, or from about 18 to about 32 deciliters/gram.

The nominal molecular weight of UHMWPE is empirically related to the intrinsic viscosity of the polymer according to the equation:

$$M(UHMWPE) = 5.3 \times 10^4 [\eta]^{1.37}$$

where M(UHMWPE) is the nominal molecular weight and $[\eta]$ is the intrinsic viscosity of the UHMW polyethylene expressed in deciliters/gram.

As used herein, intrinsic viscosity is determined by extrapolating to zero concentration the reduced viscosities or the inherent viscosities of several dilute solutions of the UHMWPE where the solvent is freshly distilled decahydronaphthalene to which 0.2 percent by weight, 3,5-di-tert-butyl-4-hydroxyhydrocinnamic acid, neopentanetetrayl ester [CAS Registry No. 6683-19-8] has been added. The reduced viscosities or the inherent viscosities of the UHMWPE are ascertained from relative viscosities obtained at 135° C. using an Ubbelohde No. 1 viscometer in accordance with the general procedures of ASTM D 4020-81, except that several dilute solutions of differing concentration are employed. ASTM D 4020-81 is, in its entirety, incorporated herein by reference.

In one particular example, the matrix comprises a mixture of substantially linear ultrahigh molecular weight polyethylene having an intrinsic viscosity of at least 10 deciliters/gram, and lower molecular weight polyethylene (LMWPE) having an ASTM D 1238-86 Condition E melt index of less than 50 grams/10 minutes and an ASTM D 1238-86 Condition F melt index of at least 0.1 gram/10 minutes. The nominal molecular weight of LMWPE is lower than that of the UHMWPE. LMWPE is thermoplastic and many different types are known. One method of classification is by density, expressed in grams/cubic centimeter and rounded to the nearest thousandth, in accordance with ASTM D 1248-84 (reapproved 1989), as summarized as follows:

TABLE 1

| Type | Abbreviation | Density (g/cm3) |
| --- | --- | --- |
| Low Density Polyethylene | LDPE | 0.910-0.925 |
| Medium Density Polyethylene | MDPE | 0.926-0.940 |
| High Density Polyethylene | HDPE | 0.941-0.965 |

Any or all of these polyethylenes may be used as the LMWPE in the present invention. For some applications, HDPE, may be used because it ordinarily tends to be more linear than MDPE or LDPE. ASTM D 1248-84 (Reapproved 1989) is, in its entirety, incorporated herein by reference.

Processes for making the various LMWPE's are well known and well documented. They include the high pressure process, the Phillips Petroleum Company process, the Standard Oil Company (Indiana) process, and the Ziegler process.

The ASTM D 1238-86 Condition E (that is, 190° C. and 2.16 kilogram load) melt index of the LMWPE is less than about 50 grams/10 minutes. Often the Condition E melt index is less than about 25 grams/10 minutes. Typically, the Condition E melt index is less than about 15 grams/10 minutes.

The ASTM D 1238-86 Condition F (that is, 190° C. and 21.6 kilogram load) melt index of the LMWPE is at least 0.1 gram/10 minutes. In many cases the Condition F melt index is at least about 0.5 gram/10 minutes. Typically, the Condition F melt index is at least about 1.0 gram/10 minutes. ASTM D 1238-86 is, in its entirety, incorporated herein by reference.

Sufficient UHMWPE and LMWPE should be present in the matrix to provide their properties to the membrane 12. Other thermoplastic organic polymers may also be present in the matrix so long as their presence does not materially affect the properties of the membrane 12 in an adverse manner. One or more other thermoplastic polymers may be present in the matrix. The amount of the other thermoplastic polymer which may be present depends upon the nature of such polymer. Examples of thermoplastic organic polymers which may optionally be present include, but are not limited to, poly(tetrafluoroethylene), polypropylene, copolymers of ethylene and propylene, copolymers of ethylene and acrylic acid, and copolymers of ethylene and methacrylic acid. If desired, all or a portion of the carboxyl groups of carboxyl containing copolymers may be neutralized with sodium, zinc, or the like.

In some examples the UHMWPE and the LMWPE together constitute at least about 65 percent by weight of the polymer of the matrix. In some examples, the UHMWPE and the LMWPE together constitute at least about 85 percent by weight of the polymer of the matrix. In some examples, the other thermoplastic organic polymers are substantially absent so that the UHMWPE and the LMWPE together constitute substantially 100 percent by weight of the polymer of the matrix. In some examples, the UHMWPE constitutes substantially all of the polymer of the matrix (e.g., LMWPE is not included in the formulation).

The UHMWPE may constitute at least one percent by weight of the polymer of the matrix. Where the UHMWPE and the LMWPE together constitute 100 percent by weight of the polymer of the matrix of the membrane 12, the UHMWPE may constitute greater than or equal to 40 percent by weight of the polymer of the matrix, such as greater than or equal to 45 percent by weight, or greater than or equal to 48 percent by weight, or greater than or equal to 50 percent by weight, or greater than or equal to 55 percent by weight of the polymer of the matrix. Also, the UHMWPE may constitute less than or equal to 99 percent by weight of the polymer of the matrix, such as less than or equal to 80 percent by weight, or less than or equal to 70 percent by weight, or less than or equal to 65 percent by weight, or less than or equal to 60 percent by weight of the polymer of the matrix. The level of UHMWPE comprising the polymer of the matrix may range between any of these values inclusive of the recited values.

Likewise, where the UHMWPE and the LMWPE together constitute 100 percent by weight of the polymer of the matrix of the membrane 12, the LMWPE may constitute greater than or equal to 1 percent by weight of the polymer of the matrix, such as greater than or equal to 5 percent by weight, or greater than or equal to 10 percent by weight, or greater than or equal to 15 percent by weight, or greater than or equal to 20 percent by weight, or greater than or equal to 25 percent by weight, or greater than or equal to 30 percent by weight, or greater than or equal to 35 percent by weight, or greater than or equal to 40 percent by weight, or greater than or equal to 45 percent by weight, or greater than or equal to 50 percent by weight, or greater than or equal to 55 percent by weight of the polymer of the matrix. Also, the LMWPE may constitute less than or equal to 70 percent by weight of the polymer of the matrix, such as less than or equal to 65 percent by weight, or less than or equal to 60 percent by weight, or less than or equal to 55 percent by weight, or less than or equal to 50 percent by weight, or less than or equal to 45 percent by weight of the polymer of the matrix. The level of the LMWPE may range between any of these values inclusive of the recited values.

It should be noted that for any of the previously described membranes 12 of the present invention, the LMWPE may comprise high density polyethylene. The membrane 12 may also include finely divided, particulate filler distributed throughout, as later described. The membrane 12 may also include minor amounts of other materials. Minor amounts may be less than or equal to 10 percent by weight, based on total weight of the membrane 12, particulate filler and other materials. The other materials used in processing, may be lubricants, processing plasticizers, organic extraction liquids, water, and the like. Further other materials introduced for particular purposes, such as thermal, ultraviolet and dimensional stability, may optionally be present in the membrane 12 in small amounts, e.g., less than or equal to 15 percent by weight, based on total weight of the membrane 12, particulate filler, and other materials. Examples of such further materials include, but are not limited to, antioxidants, ultraviolet light absorbers, reinforcing fibers such as chopped glass fiber strand, and the like. The balance of the membrane 12, exclusive of filler and any coating, printing ink, or impregnant applied for one or more special purposes is essentially the thermoplastic organic polymer.

Finely Divided, Particulate Filler

As previously mentioned, the membrane 12 may include finely divided, particulate filler distributed through the membrane 12. In one example, the particulate filler includes siliceous particles having particulate silica. The particulate filler may include an organic particulate material and/or an inorganic particulate material. The particulate filler may or may not be colored. For example, the particulate filler material may be a white or off-white particulate filler material, such as siliceous or clay particulate material. The particulate filler may be substantially water-insoluble filler particles. Substantially water-insoluble means having <50 mg/L solubility in pure water at 25° C.

The finely divided substantially water-insoluble filler particles may constitute from 10 to 90 percent by weight of the membrane 12, the filler particles, and other materials (excluding coating applied to the membrane 12). For example, such filler particles may constitute from 20 percent to 90 percent by weight of the membrane 12, the filler particles, and other materials (excluding coating applied to the membrane 12), such as from 30 percent to 70 percent, or such as from 40 percent to 60 percent.

The finely divided, particulate filler may be in the form of ultimate particles, aggregates of ultimate particles, or a combination of both. At least about 90 percent by weight of the particulate filler used in preparing the membrane 12 may have gross particle sizes in the range of from 0.5 to about 200 micrometers, such as from 1 to 100 micrometers, as determined by the use of a laser diffraction particle size instrument, LS230 from Beckman Coulton, which is capable of measuring particle diameters as small as 0.04 micrometers. At least 90 percent by weight of the particulate filler may have a gross particle sizes in the range of from 5 to 40, e.g., 10 to 30 micrometers. The sizes of the particulate filler agglomerates may be reduced during processing of the ingredients used to prepare the membrane 12. Accordingly, the distribution of gross particle sizes in the membrane 12 may be smaller than in the raw filler itself.

Non-limiting examples of suitable organic and inorganic particulate filler that may be used in the membrane 12 of the present invention may include those described in U.S. Pat. No. 6,387,519 B1 at column 9, line 4 to column 13, line 62, the cited portions of which are incorporated herein by reference.

In a particular embodiment of the present invention, the particulate filler material includes siliceous materials. Non-limiting examples of siliceous fillers that may be used to prepare the microporous material include silica, mica, montmorillonite, kaolinite, nanoclays such as cloisite, which is available from Southern Clay Products (Gonzales, Tex.), talc, diatomaceous earth, vermiculite, natural and synthetic zeolites, calcium silicate, aluminum silicate, sodium aluminum silicate, aluminum polysilicate, alumina silica gels and glass particles. In addition to the siliceous fillers, other finely divided particulate substantially waterinsoluble fillers optionally may also be employed. Non-limiting examples of such optional particulate fillers include carbon black, charcoal, graphite, titanium oxide, iron oxide, copper oxide, zinc oxide, antimony oxide, zirconia, magnesia, alumina, molybdenum disulfide, zinc sulfide, barium sulfate, strontium sulfate, calcium carbonate, and magnesium carbonate. Some of such optional fillers are color-producing fillers and, depending on the amount used, may add a hue or color to the microporous material. In a non-limiting embodiment, the siliceous filler may include silica and any of the aforementioned clays. Non-limiting examples of silicas include precipitated silica, silica gel, fumed silica, and combinations thereof.

Silica gel is generally produced commercially by acidifying an aqueous solution of a soluble metal silicate, e.g., sodium silicate, at low pH with acid. The acid employed is generally a strong mineral acid such as sulfuric acid or hydrochloric acid, although carbon dioxide can be used. Inasmuch as there is essentially no difference in density between the gel phase and the surrounding liquid phase while the viscosity is low, the gel phase does not settle out, that is to say, it does not precipitate. Consequently, silica gel may be described as a non-precipitated, coherent, rigid, three-dimensional network of contiguous particles of colloidal amorphous silica. The state of subdivision ranges from large, solid masses to submicroscopic particles, and the degree of hydration from almost anhydrous silica to soft gelatinous masses containing on the order of 100 parts of water per part of silica by weight.

Precipitated silica generally is produced commercially by combining an aqueous solution of a soluble metal silicate, ordinarily alkali metal silicate such as sodium silicate, and an acid so that colloidal particles of silica will grow in a weakly alkaline solution and be coagulated by the alkali metal ions of the resulting soluble alkali metal salt. Various acids may be used, including but not limited to mineral acids. Non-limiting examples of acids that may be used include hydrochloric acid and sulfuric acid, but carbon dioxide can also be used to produce precipitated silica. In the absence of a coagulant, silica is not precipitated from solution at any pH. In a non-limiting embodiment, the coagulant used to effect precipitation of silica may be the soluble alkali metal salt produced during formation of the colloidal silica particles, or it may be an added electrolyte, such as a soluble inorganic or organic salt, or it may be a combination of both.

Many different precipitated silicas can be employed as the siliceous filler used to prepare the microporous material. Precipitated silicas are well-known commercial materials, and processes for producing them are described in detail in many United States patents, including U.S. Pat. Nos. 2,940,830 and 4,681,750. The average ultimate particle size (irrespective of whether or not the ultimate particles are agglomerated) of precipitated silica used to prepare the microporous material is generally less than 0.1 micrometer, e.g., less than 0.05 micrometer or less than 0.03 micrometer, as determined by transmission electron microscopy. Precipitated silicas are available in many grades and forms from PPG Industries, Inc. (Pittsburgh, Pa.). These silicas are sold under the Hi-Sil trademark.

For purposes of the present invention, the finely divided particulate siliceous filler can make up at least 50 percent by weight, e.g., at least 65 or at least 75 percent by weight, or at least 90 percent by weight of the particulate filler material. The siliceous filler may make up from 50 to 90 percent by weight, e.g., from 60 to 80 percent by weight, of the particulate filler, or the siliceous filler may make up substantially all (over 90 percent by weight) of the particulate filler.

The particulate filler, e.g., the siliceous filler, typically has a high surface area, which allows the filler to carry much of the processing plasticizer composition used to produce the microporous material of the present invention. High surface area fillers are materials of very small particle size, materials that have a high degree of porosity, or materials that exhibit both of such properties. The surface area of the particulate filler, e.g., the siliceous filler particles, can range from 20 to 1000 square meters per gram, e.g., from 25 to 400 square meters per gram, or from 40 to 200 square meters per gram, as determined by the Brunauer, Emmett, Teller (BET) method according to ASTM D 1993-91. The BET surface area is determined by fitting five relative pressure points from a nitrogen sorption isotherm measurement made using a Micromeritics Tri Star3000™ instrument. A FlowPrep-060™ station can be used to provide heat and continuous gas flow during sample preparation. Prior to nitrogen sorption, silica samples are dried by heating to 160° C. in flowing nitrogen (PS) for 1 hour. The surface area of any non-siliceous filler particles used may also be within one of these ranges. The filler
particles may be substantially water-insoluble and may also be substantially insoluble in any organic processing liquid used to prepare the microporous material. Substantially waterinsoluble means having <50 mg/L solubility in pure water at 25° C. Substantially insoluble in an organic processing liquid means having <50 mg/L solubility in the organic processing liquid. This may facilitate retention of the particulate filler within the microporous material. The membrane 12 may also include a network of interconnecting pores, which communicate substantially throughout the membrane 12. On a coating-free, printing ink free and impregnant-free basis, pores typically constitute from 35 to 95 percent by volume, based on the total volume of the membrane 12, when made by the processes as further described herein. The pores may constitute from 60 to 75 percent by volume of the membrane 12, based on the total volume of the microporous material. As used herein, the porosity (also known as void volume) of the membrane 12, expressed as percent by volume, is determined according to the following equation:
Porosity=100[1−d1/d2] where, d1 is the density of the sample, which is determined from the sample weight and the sample volume as ascertained from measurements of the sample dimensions; and d2 is the density of the solid portion of the sample, which is determined from the sample weight and the volume of the solid portion of the sample. The volume of the solid portion of the microporous material is determined using a Quantachrome stereopycnometer (Quantachrome Instruments (Boynton Beach, Fla.)) in accordance with the operating manual accompanying the instrument.

The volume average diameter of the pores of the membrane 12 is determined by mercury porosimetry using an Autoscan mercury porosimeter (Quantachrome Instruments (Boynton Beach, Fla.)) in accordance with the operating manual accompanying the instrument. The volume average pore radius for a single scan is automatically determined by the porosimeter. In operating the porosimeter, a scan is made in the high pressure range (from 138 kilopascals absolute to 227 megapascals absolute). If 2 percent or less of the total intruded volume occurs at the low end (from 138 to 250 kilopascals absolute) of the high pressure range, the volume average pore diameter is taken as twice the volume average pore radius determined by the porosimeter. Otherwise, an additional scan is made in the low pressure range (from 7 to 165 kilopascals absolute) and the volume average pore diameter is calculated according to the equation:

$$d=2[v1r1/w1+v2r2/w2]/[v1/w1+v2/w2]$$

where, d is the volume average pore diameter; v1 is the total volume of mercury intruded in the high pressure range; v2 is the total volume of mercury intruded in the low pressure range; r1 is the volume average pore radius determined from the high pressure scan; r2 is the volume average pore radius determined from the low pressure scan; w3 is the weight of the sample subjected to the high pressure scan; and w2 is the weight of the sample subjected to the low pressure scan.

Generally on a coating-free, printing ink-free and impregnant-free basis, the volume average diameter of the pores (mean pore size) of the membrane 12 may be up to 0.5 micrometers, such as up to 0.3 micrometers, or up to 0.2 micrometers. The average diameter of the pores may be at least 0.02 micrometers, such as at least 0.04 micrometers, or at least 0.05 micrometers. The volume average diameter of the pores, on this basis, may range between any of these values, inclusive of the recited values. For example, the volume average diameter of the pores of the membrane 12 may range from 0.02 to 0.15 micrometers, or from 0.02 to 0.1 micrometers, or from 0.02 to 0.075 micrometers, in each case inclusive of the recited values.

In the course of determining the volume average pore diameter by means of the above described procedure, the maximum pore radius detected may also be determined. This is taken from the low pressure range scan, if run; otherwise it is taken from the high pressure range scan. The maximum pore diameter of the microporous material is typically twice the maximum pore radius.

Coating, printing and impregnation processes may result in filling at least some of the pores of the membrane 12. In addition, such processes may also irreversibly compress the membrane 12. Accordingly, the parameters with respect to porosity, volume average diameter of the pores, and maximum pore diameter are determined for the membrane 12 prior to application of one or more of these processes. The membrane 12, including the finely divided, particulate filler and/or other materials (excluding coating applied to the membrane 12) may have a density between 0.4 g/cm3 and 1.0 g/cm3. The density can range between any of the above-stated values, inclusive of the recited values. As used herein and in the claims, the density of the membrane 12 is determined by measuring the weight and volume of a sample of the microporous material.

The porosity of the membrane 12 may be measured in terms of the rate of air flow through a sample, herein measured and reported as Gurley porosity. The Gurley porosity of the membrane 12, including the finely divided, particulate filler and/or other materials (excluding coating applied to the membrane 12) may be greater than 15 seconds, such as greater than 100 seconds, greater than 200 seconds, greater than 300 seconds, greater than 400 seconds, or greater than 500 seconds. Gurley porosity is determined using a Gurley densometer, model 4340, manufactured by GPI Gurley Precision Instruments of (Troy, N.Y.) The Gurley porosity reported was a measure of the rate of air flow through a sample or it's resistance to an air flow through the sample. The unit of measure is a "Gurley second" and represents the time in seconds to pass 100 cc of air through a 1 inch square (6.4×10-4 m2) area using a pressure differential of 4.88 inches of water (12.2×102 Pa). Lower values equate to less air flow resistance (more air is allowed to pass freely). The measurements were completed using the procedure listed in the manual, MODEL 4340 Automatic Densometer and Smoothness Tester Instruction Manual. TAPPI method T 460 om-06-Air Resistance of Paper may also be referenced for the basic principles of the measurement.

Volatile Composition

In an exemplary embodiment, the volatile composition 9 may be configured such that the composition 9 comprises at least 20% of perfume raw materials having an average vapor pressure at 25 degrees Celsius of greater than or equal to 0.01 torr.

The volatile composition 9 may comprise one or more perfume compounds, or a mixture of perfume compounds. The volatile composition 9 can be in the form of perfume oil and can include one or more essential oils, volatile organic compounds, or mixtures thereof. Furthermore, the volatile composition 9 can include synthetically or naturally formed materials. Examples include, but are not limited to: oil of bergamot, bitter orange, lemon, mandarin, caraway, cedar leaf, clove leaf, cedar wood, geranium, lavender, orange, origanum, petitgrain, white cedar, patchouli, neroili, rose absolute, and the like.

The volatile composition 9 may alternatively be in the form of a crystalline solid, which has the ability to sublime into the vapor phase at ambient temperatures or be used to fragrance a liquid. Any suitable crystalline solid in any suitable amount or form may be used. For example, suitable crystalline solids include but are not limited to: vanillin, ethyl vanillin, coumarin, tonalid, calone, heliotropene, musk xylol, cedrol, musk ketone benzohenone, raspberry ketone, methyl naphthyl ketone beta, phenyl ethyl salicylate, veltol, maltol, maple lactone, proeugenol acetate, evemyl, and the like.

In the case of air freshener or fragrances, different volatile materials can be used together that are similar, related, complementary, and/or contrasting. In addition to volatile materials, the apparatus 1 may include any known compounds configured to neutralize odors.

The volatile composition may, optionally, include odor masking agents, odor blocking agents, and/or diluents. "Odor blocking" refers to the ability of a compound to dull the human sense of smell. "Odor-masking" refers to the ability of a compound to mask or hide a malodorous compound. Odor-masking may include a compound with a non-offensive or pleasant smell that is dosed such it limits the ability to sense a malodorous compound. Odor-masking may involve the selection of compounds which coordinate with an anticipated malodor to change the perception of the overall scent provided by the combination of odorous compounds. Exemplary diluents include dipropylene glycol methyl ether, and 3-methoxy-3-methyl-1-butanol, and mixtures thereof. The volatile composition may also, optionally, include perfume raw materials that solely provide a hedonic benefit (i.e. perfume raw materials which do not prevent mold yet provide a pleasant fragrance). The volatile composition 9 may be comprised in an apparatus 1 as shown in the figures according to the present invention. For the purposes of illustrating the present invention in detail, the invention is described below in connection with automobiles. However, it will be appreciated that the invention may be implemented in any interior occupancy space employing an HVAC system.

Figure 6A:
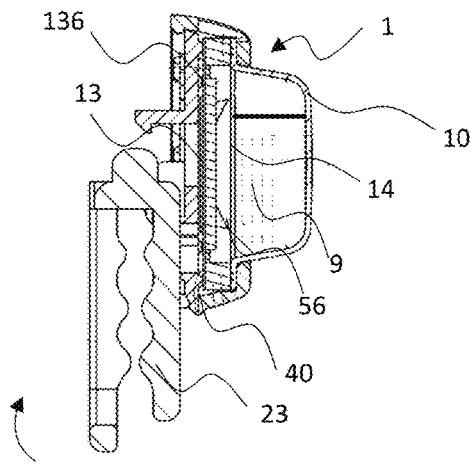
FIG. 6A is a side section view of the apparatus shown in FIG. 5 when it is assembled before activation.
Figure 6B:
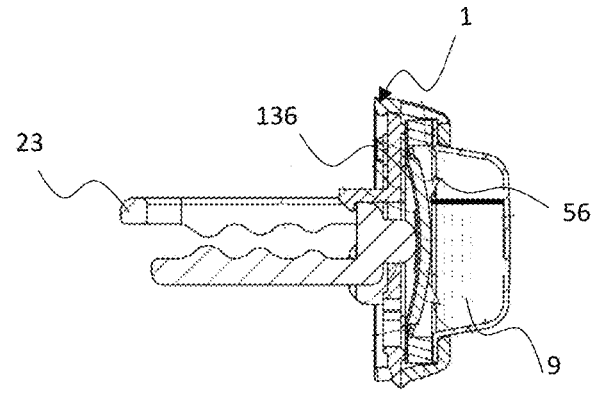
FIG. 6B is a side section view of the apparatus of FIG. 6A after activation.

Referring to FIG. 1, the vapor impermeable substrate 14 may be releasably attached to a periphery of the membrane 13 to form a removeable cover for the apparatus 1. The vapor impermeable substrate 14 may be rupturable to allow the volatile composition 12 to pass through when ruptured. For example, as shown in FIGS. 6A and 6B, the vapor impermeable substrate 14 may be a rupturable substrate disposed adjacent to the composite membrane 13 and attached to an inner periphery of the container 10 to form a sealed reservoir adjacent the membrane 13.

The apparatus 1 may be configured for use in any desired orientation, including but not limited to a vertical orientation such as shown in FIG. 2. FIG. 2 shows a side schematic view of the apparatus 1 of FIG. 1 wherein the apparatus 1 is substantially the same as the apparatus 1 of FIG. 1 except that when the apparatus 1 is in use, the membrane 13 comprises a first side 134 disposed in fluid communication with the volatile composition 12 and a second side 136 facing the environment and away from the volatile composition 12 when the vapor impermeable substrate 14 is removed when the user needs to activate the apparatus 1.

The method of the present invention may be directed to a method of controlled release of a volatile composition in an interior occupancy space, the method comprising the steps of:

operably connecting an apparatus 1 of the present invention to a mounting portion; and attaching the mounting portion to an air vent 33.

The apparatus 1 of the present invention can be configured for use in a variety of applications to deliver a volatile composition 9 to the atmosphere and/or a surface.

Accordingly, the specific physical properties of the membrane 13 may be chosen based on the specific desired use of the apparatus 1, designed to be activated by peeling off the vapor impermeable substrate 14 or by rupturing the vapor impermeable substrate 14. Examples of suitable physical parameters of the vapor impermeable substrate 14 suitable for an apparatus 1 designed to be activated by rupturing the vapor impermeable substrate 14 will be described hereinafter in the description.

The vapor impermeable substrate 14 may be made of any material that can be ruptured with a pre-determined applied force, with or without the presence of an element, such as rupture element, to aid in such rupture. In embodiments where the vapor impermeable substrate 40 is intended to contain the volatile composition when the apparatus 1 is not in use, the vapor impermeable substrate 40 may be made from any suitable barrier material that reduces or prevents evaporation of the volatile composition 12. Such materials may be impermeable to vapors and liquids. Suitable barrier materials for the vapor impermeable substrate 40 include, but are not limited to coated or uncoated films, such as polymeric films, webs, foils, and composite materials such as foil/polymeric film laminates. An example of a foil that may be used as a barrier material is a micron aluminum foil including a nitrocellulose protective lacquer, a polyurethane primer, and a 15 g/m2 polyethylene coating (Lidfoil 118-0092), available from Alcan Packaging. Suitable polymeric films include, but are not limited to, polyethylene terephtalate (PET) films, acrylonitrile copolymer barrier films such as, for example, those sold under the tradename Barex® by INOES, ethylene vinyl alcohol films, and combinations thereof. It is also contemplated that coated barrier films may be utilized as the vapor impermeable substrate 14. Such coated barrier films include, but are not limited to, metallized PET, metalized polypropylene, silica or alumina coated film.

Figure 5:
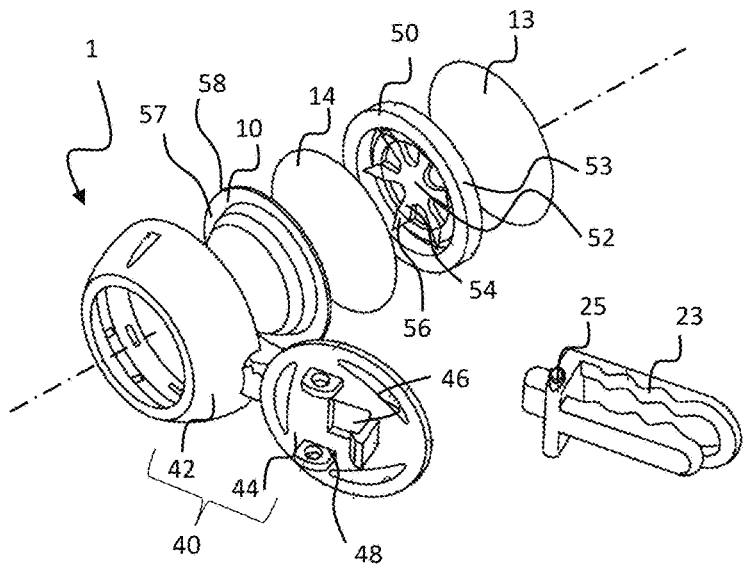
FIG. 5 is a perspective view of components of a variation of an apparatus according to the present invention.

FIG. 5 is a perspective view of components in a variation of an apparatus 1 according to the present invention. The apparatus 1 of FIG. 5 comprise substantially the same features as the apparatus 1 of FIG. 1 with additional components described as follows.

Figure 7:
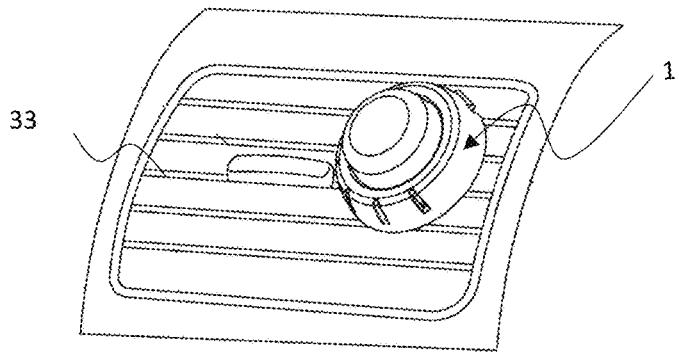
FIG. 7 is a front perspective view of the apparatus of FIGS. 6A and 6B in use in an automobile environment.

Referring to FIG. 5, the apparatus 1 comprises a housing 40 having a front cover 42 and a rear frame 44, the front cover 42 and the rear frame 44 defining an interior space. The rear frame 44 may comprise a pair of lugs 48 disposed adjacent a frame opening 46 and extending from the rear frame 44. The lugs 48 may be shaped and sized to engage with pins 25 extending from a mounting portion 23. The mounting portion 23 may be attached to, movably attached to, rotatably attached to, or pivotally attached to the apparatus 1. In an exemplary example, the mounting portion 23 may be an actuator 23 configured to be movable relative to the housing 40 for activating the apparatus 1. In that example, the rear frame 44 may be provided with the frame opening 46 located substantially in the center of the rear frame 44. The mounting portion 23 may be configured as a movable or resilient clip for attaching the apparatus 1 to an air vent 33 as shown in FIG. 7.

When the volatile composition 12 is a liquid volatile composition, the apparatus 1 may comprise a rupturable vapor impermeable substrate 14 sealably attached to and covering the reservoir 11 to prevent the volatile composition 12 from being released until the apparatus 1 is activated. The rupturable vapor impermeable substrate 14 may be ruptured to release the volatile composition 12 by actuating a rupture mechanism 50 positioned adjacent to the rupturable vapor impermeable substrate 14. The rupture mechanism 50 comprises a movable member 52 movably attached to an outer frame 53 by a resilient member 54. The resilient member 54 may be formed of one or more springs. One or more rupture elements 56 are arranged within the rupture mechanism 50 to puncture holes in the rupturable vapor impermeable substrate 14. The rupture element 56 may be a pin. The composite membrane 13 may be sealably attached to a flange 57 located at the periphery 58 of the container 10. The composite membrane 13 encloses the container 10, the volatile composition 12, the rupturable vapor impermeable substrate 14, and the rupture mechanism 50. The composite membrane 13 may be configured to flex when a pressure or an actuation force is applied on the composite membrane 13 through the mounting portion 23.

FIGS. 6A and 6B show the apparatus 1 of FIG. 5 in its assembled form with the volatile composition 12 and in a first position before activation (FIG. 6A) and a second position after activation (FIG. 6B). Referring to FIG. 6A, to activate the apparatus 1, a user rotates the mounting portion 23 relative to the housing 40 to move the composite membrane 13 and at least a portion of the rupture element 56 toward and to puncture the rupturable vapor impermeable substrate 14 and release at least a portion of the volatile composition 9 from the container 10 such that the portion of the volatile composition 9 evaporates from the apparatus 1. It will be appreciated that the mounting portion 23 may be configured using known mechanical methods to move linearly or in a rotary motion so as to move the composite membrane 13 and at least a portion of the rupture element 56 toward and to puncture the rupturable vapor impermeable substrate 14. Once the rupturable vapor permeable substrate 14 is pierced, the volatile composition 9 flows out of the container 10, wets the composite membrane 13 and is then delivered to the atmosphere surroundings through evaporation from the composite membrane 13 via the second side 136. The composite membrane 13 is configured to prevent the liquid phase of the volatile composition 9 from flowing out of the composite membrane 13 but enables vaporization of a vapor phase of the volatile composition 9 from the second side 136 so that the volatile composition 9 is delivered to the environment.

The following examples are intended to more fully illustrate the present invention and are not to be construed as limitations of the present invention since many variations thereof are possible without departing from the scope of the present invention. All parts, percentages and ratios used herein are expressed as percent weight unless otherwise specified.

EXAMPLES

Test equipment/materials and test volatile compositions are first described under Materials, then Test Methods are provided, and lastly results are discussed. Data is provided demonstrating the apparatus 1 of the present invention having reduced vapor release rate when used in an air conditioning system. Equipment and materials used in the Test Methods described hereinafter are listed in Table 2 below. The inventive and comparative examples are provided in Table 3 below. The volatile compositions used in the examples are prepared using conventional methods.

Materials

TABLE 2

| | Equipment/Materials |
|---|---|
| Example | Materials/Details |
| Fan (Example to simulate fan of an air conditioning system in an automobile) | SONA 7" Desk & Clip fan Model No. SFD1218 VOLT 220-240 V 50 Hz Watt 25 W |

TABLE 2-continued

Equipment/Materials

| Example | Materials/Details |
|---|---|
| Anemometer for measuring air flow rate | Testo 425 Thermal Anemometer |
| Comparative Air Freshener Example 1 ("Comparative Example 1") | Air Freshener Components as shown in FIG. 5<br>Microporous membrane (Commercially available as Teslin HD1100) of Table 4<br>Volatile composition 1 |
| Comparative Air Freshener Example 2 ("Comparative Example 2") | Air Freshener Components as shown in FIG. 5<br>Microporous membrane (Commercially available from PPG Industries as Teslin HD1100) of Table 4<br>Inventive Volatile composition 1 of Table 3 |
| Inventive Air Freshener Example 2 ("Inventive Example 2") | Air Freshener Components as shown in FIG. 5<br>Composite membrane sample 1 of Table 4<br>Inventive Volatile composition 1 of Table 3 |
| Inventive Air Freshener Example ("Inventive Example 3") | Air Freshener Components as shown in FIG. 5<br>Composite membrane sample 2 of Table 4<br>Volatile composition 1 of Table 3 |
| Inventive Air Freshener Example ("Inventive Example 4") | Air Freshener Components as shown in FIG. 5<br>Composite membrane sample 3 of Table 4<br>Volatile composition 1 of Table 3 |
| Inventive Air Freshener Example ("Inventive Example 5") | Air Freshener Components as shown in FIG. 5<br>Composite membrane sample 2 of Table 4<br>Volatile composition 2 of Table 3 |
| Inventive Air Freshener Example ("Inventive Example 6") | Air Freshener Components as shown in FIG. 5<br>Composite membrane sample 3 of Table 4<br>Volatile composition 2 of Table 3 |

Air Freshener Example Preparation

Inventive Examples are prepared according to the following steps:

1. Using a heat sealer at 380 deg F., 50 psig and 3 s, attach the uncoated side of the composite membrane on a polyethylene-based thermoform container having a reservoir (see container 10 of FIG. 5). The effective membrane area (evaporative surface area) of the composite membrane is 7 cm$^2$.
2. Add 2.4 ml of a volatile composition to the prepared membrane sealed thermoform container.
3. Place the thermoform reservoir containing the volatile composition inside an apparatus as shown in FIG. 5.

Comparative Examples are prepared according to the above steps and differs in that the membrane used is uncoated.

For the test methods/calculations described hereinafter, any volatile composition suitable for use in air fresheners or vapor phase systems may be employed. For illustrative purposes as well as for the subsequent examples, the volatile composition is a perfume composition as shown in the formulation of Table 3 below. The volatile composition, however, may constitute any number of materials suitable for air freshening as long as at least 20% of the perfume raw materials have an average vapor pressure greater than or equal to 0.01 torr at 25 degrees Celsius.

TABLE 3

| Perfume Raw Materials | | Inventive Volatile | Inventive Volatile |
|---|---|---|---|
| Vapor Pressure 25° C. Low | Vapor Pressure 25° C. High | Composition 1 % of perfume raw materials by weight of the composition | Composition 2 % of perfume raw materials by weight of the composition |
| 0.00001 | 0.001 | 0.078 | 0.932 |
| 0.001 | 0.01 | 16.833 | 13.992 |
| 0.01 | 0.1 | 30.538 | 38.505 |
| 0.1 | 0.3 | 29.028 | 25.969 |
| 0.3 | 10 | 23.523 | 20.602 |

Preparation of Composite Membranes

Table 4 describes the comparative membrane (non-coated membrane) and inventive composite membrane (coated membrane) examples which are evaluated in Examples I and II.

TABLE 4

| | First Side 134 | Second Side 136 | Substrate/Membrane 12 |
|---|---|---|---|
| Composite Membrane Sample 1 Membrane Structure as shown in FIG. 3B | Uncoated | Coating Structure: Material 2B on Substrate followed by Material 2C on Material 2B as shown in FIG. 4C<br>Material 2B: SELVOL ® 325 polyvinyl alcohol, Sekisui Specialty Chemicals America (Dallas, TX)<br>Coating Weight of 2B: Not disclosed by manufacturer<br>Material 2C: UNIDYNE ® 8112 Daikin America, Inc)]<br>Material Coating weight of 2C: not disclosed by manufacturer | Teslin HD1100 |

TABLE 4-continued

| | First Side 134 | Second Side 136 | Substrate/Membrane 12 |
|---|---|---|---|
| Composite Membrane Sample 2 Membrane Structure as shown in FIG. 3B | Uncoated | Coating Structure: Material 2B on Substrate followed by Material 2C on Material 2B as shown in FIG. 4C Material 2B: SELVOL ® 325 polyvinyl alcohol, Sekisui Specialty Chemicals America (Dallas, TX) Coating weight Material 2C: UNIDYNE ® 8112 Daikin America, Inc)] Material Coating weights not disclosed by manufacturer | Teslin HD1100 |
| Composite Membrane Sample 3 Membrane Structure as shown in FIG. 3B | Uncoated | Coating Structure: Material 2B on Substrate followed by Material 2C on Material 2B as shown in FIG. 4C Material 2B: SELVOL ® 325 polyvinyl alcohol, Sekisui Specialty Chemicals America (Dallas, TX) Material 2C: UNIDYNE ® 8112 Daikin America, Inc)] Material Coating weights not disclosed by manufacturer | Teslin HD1100 |
| Commercially Available Membrane Teslin HD1100 | Uncoated | Uncoated | Teslin HD1100 |

In Example III, Membrane Comparative Examples are left uncoated, or coated with hydrophilic coatings only. Comparative Example 11 ("CE-11") and Comparative Example 12 ("CE-12") are both treated with Composition 2A as described above. CE-12 is coated on Side A (corresponding to first side 134 of FIG. 2) with an additional hydrophilic solution, 2B, which is applied in the same manner as described for composition 2C above. Comparative Example 13 is provided, which is a PVDF membrane fused with a super hydrophobic composition. This material is commercially available as DURAPEL® GVSP, available from MilliporeSigma (Billerica, Mass.).

Composite membranes are prepared according to the following steps:

Step 1. Preparation of Coating Solutions

Hydrophilic Coating Composition 2A

Poly (2-ethyl-2-oxazoline), (20 g, weight average molecular weight (Mw)~50,000) is dispersed in cool water (910 g) under mild agitation in a 4000 mL beaker. The mixture is stirred for 4 hours, followed by addition of PLURONIC®17R2 (10 g, a Block Copolymer Surfactant available from BASF (Ludwigshafen, Germany)) and 2-butoxyethanol (60 g), after which the resultant solution is stirred for an additional 30 minutes.

Hydrophilic Coating Composition 2B

SELVOL® 325 (4 g, polyvinyl alcohol available from Sekisui Specialty Chemicals America (Dallas, Tex.)) is dispersed in cool water (96 g) under mild agitation in a 300 mL beaker using a 1 inch (2.54 cm) paddle stirrer driven by an electric stir motor. The mixture is heated to 190° F. (87.8° C.) and stirred for approximately 25 minutes until completely dissolved. The resultant solution is cooled to room temperature with stirring.

Hydrophobic/Oleophobic Coating Composition 2C

UNIDYNE® 8112 (15 g, available from Daikin America, Inc. (Orangeburg, N.Y.)) is dispersed in cool water (85 g) under mild agitation in a 400 mL beaker.

Step 2. Coating Procedures

All membranes/substrate 12 are cut to 8.5×11-inch [0.22× 0.28 m] sheets prior to treatment with any coating composition. In each case, the 8.5×11-inch [0.22×0.28 m] sheet is placed on a clean glass surface and taped along the short side.

Each of the composite membrane samples are prepared according to the following steps:

1. Each substrate is taped on a balance prior to placing the sheet, Side B facing up, on a clean glass surface and using tape to adhere the top corners of the sheet to the glass.
2. A piece of clear 10 mil thick polyester 11 inch (0.28 m)×3 inch (0.08 m) is positioned to overlap across the top edge of the sheet and affixed to the glass surface with tape.
3. A wire wrapped metering rod #3 from Diversified Enterprises is placed on the polyester near the top edge.
4. A 10 to 20 mL quantity of coating is deposited as a bead strip (approximately ¼ inch (0.64 cm) wide) directly next to and touching the metering rod using a disposable pipette.
5. The bar is drawn down across the sheet at approximately a constant rate.
6. The resultant wet sheet is removed from the glass surface, immediately placed on the previously tared balance, weighed, then placed in a forced air oven and dried at 95° C. for 2 minutes.
7. The dried sheet is removed from oven and the same coating procedure was repeated on Side B such that the membrane 12 is coated with hydrophilic composition 2B on second side 136 only (Side B) first and hydrophobic/oleophobic composition 2C is applied to the hydrophilic composition 2B on the side 136 to form a diffusion regulating coating 138.
8. The coated microporous material is then clamped on an aluminum frame which is fitted with a gasket to prevent the film from shrinking during drying.

9. The framed membrane is then dried in an oven at 95° C. for 15 minutes.

It will be appreciated that the above coating procedure can be modified to achieve the composite membranes as described in Example III or as described hereinafter in the description.

Test Methods/Calculation(s)

A. Physical Properties Testing of Membranes

Each of the membranes, treated membranes ("composite membranes"), and comparative untreated membranes are characterized by testing the physical properties described below according to the test methods described hereinafter.

A1. Gurley Porosity Test Method

The Gurley Porosity Test Method is performed on dry membrane samples. Porosity is determined using a Gurley Precision Densometer, model 4340, manufactured by GPI Gurley Precision Instruments (Troy, N.Y.). The Porosity reported is a measure of the rate of air flow through a sample or it's resistance to an air flow through the sample. The unit of measure is a "Gurley second" and represents the time in seconds to pass 100 cc of air through a 1 inch square area using a pressure differential of 4.88 inches of water. Lower values equate to less air flow resistance (more air is allowed to pass freely, e.g., more porous). The measurements are completed using the procedure listed in the manual, MODEL 4340 Automatic Densometer and Smoothness Tester Instruction Manual. TAPPI method T 460 om-06-Air Resistance of Paper can also be referenced for the basic principles of the measurement.

A2. Density Test Method

The density of the above-described examples is determined by dividing the average weight of two specimens measuring 4.5×5 inches (11.43 cm×12.7 cm) that is cut from each sample by the average volume of those specimens.

A3. Pore size Test Method

The volume average diameter of the pores of the microporous material is determined by mercury porosimetry using an Autoscan mercury porosimeter (Quantachrome Instruments (Boynton Beach, Fla.)) in accordance with the operating manual accompanying the instrument. The volume average pore radius for a single scan is determined automatically by the porosimeter. In operating the porosimeter, a scan is made in the high pressure range (from 138 kilopascals absolute to 227 megapascals absolute). If 2 percent or less of the total intruded volume occurs at the low end (from 138 to 250 kilopascals absolute) of the high pressure range, the volume average pore diameter is taken as twice the volume average pore radius determined by the porosimeter. Otherwise, an additional scan is made in the low pressure range (from 7 to 165 kilopascals absolute) and the volume average pore diameter is calculated according to the equation:

$$d=2[v1r1/w1+v2r2/w2]/[v1/w1+v/w2]$$

where, d is the volume average pore diameter; v 1 is the total volume of mercury intruded in the high pressure range; v 2 is the total volume of mercury intruded in the low pressure range; r1 is the volume average pore radius determined from the high pressure scan; r2 is the volume average pore radius determined from the low pressure scan; w1 is the weight of the sample subjected to the high pressure scan; and w2 is the weight of the sample subjected to the low pressure scan.

A4. Contact Angle Test Method

The contact angle is measured on a VCA 2500XE video contact angle system, available from AST Products, Inc. (Billerica, Mass.) using 1 microliter of ultrapure water. On all samples, contact angle is measured on Side A.

A5. Oil Rating Test Method

The oil rating is measured with AATCC test method 118-2007. In cases where Sides A and B are different, the oil rating is measured on Side A wherein Side A is a side of the test membrane exposed to the interior of the reservoir.

B. Membrane Performance Test Methods

A testing apparatus is used for evaluating the following performance parameters of the test membranes. Components of an exemplary embodiment of the testing apparatus is described below wherein the testing apparatus is a holder assembly used for evaporation rate and performance testing of a membrane.

B1. Assembly of Testing Apparatus

The holder assembly consists of a front clamp with a ring gasket, a back clamp, test reservoir cup, and four screws. The test reservoir cup is fabricated from a clear thermoplastic polymer, having interior dimensions defined by a circular diameter at the edge of the open face of approximately 4 centimeters and a depth of no greater than 1 centimeter. The open face is used to determine the volatile material transfer rate. Each clamp of the holder assembly has a 1.5 inch (3.8 cm) diameter circular opening to accommodate the test reservoir cup and provide an opening to expose the membrane under test. When placing a membrane under test, the back clamp of the holder assembly is placed on top of a cork ring. The test reservoir cup is placed in the back clamp and charged with an amount of benzyl acetate as described below, used to simulate fragrance compositions.

The front clamp of the holder is carefully placed over the entire assembly, with the screw holes aligned and so as not to disturb the membrane disk. The screws are attached and tightened enough to prevent leaking. The ring gasket creates a seal. Five replicates are assembled for each membrane tested.

Air Flow Conditions

Examples tested under "non-restricted" conditions are placed laboratory chemical fume hood having approximate dimensions of 5 feet (1.52 m) (height)×5 (1.52 m) feet (width)×2 (0.61 m) feet (depth). The glass doors of the fume hood are pulled down, and the air flow through the hood are adjusted so as to have eight (8) turns (or turnovers) of hood volume per hour.

Examples tested under "restricted" conditions are placed in a HDPE enclosed box, having approximate dimensions of 11 inches (0.28 m) (height)×19 inches (0.48 m) (width)×11 inches (0.28 m) (depth). Enclosing the container is an 11×19 inch (0.28×0.48 m) cardboard sheet, wrapped with duct tape.

B2. Volatile Material Transfer Rate Test

A volatile material transfer rate of a membrane is evaluated according to the following steps:

1. Each holder assembly is weighed to obtain an initial weight of the entire charged assembly.
2. The assembly is then placed upright such that the membrane is oriented vertically and benzyl acetate is in direct contact with at least a portion of the test membrane.
3. The upright (vertically oriented) assembly is placed in an environment defined below according to the airflow, maintained at 25°±5° C. The humidity within in environment is ambient.
4. The test reservoirs are weighed every 24 hours for a minimum of 14 days.
5. The calculated weight loss of benzyl acetate over the entire time period, in combination with the elapsed time and surface area of the microporous sheet exposed to the interior of the test reservoir, is used to determine the volatile material transfer rate of the microporous sheet, in units of mg/(hour*cm2).

6. The average evaporation rate is converted to volatile material transfer rate according to the following formula:

Average Evaporation Rate (mg/hr)/12.5 cm2=Volatile Material Transfer Rate (mg/(hour*cm2))

7. The average of all evaluations over time for all replicates is used to determine the average evaporation rate of a test reservoir.

B3. Sweat Rating

A sweat rating of a test membrane is evaluated according to the following steps:

1. Concurrent with the volatile material transfer rate testing, every 24 hours for at least 14 days, the exterior membrane surface on each assembly is visually inspected for liquid accumulation.

2. The sweat rating used a numbering system, with "0" being no liquid accumulation; "1" being liquid accumulation on the substrate alone; "2" having liquid accumulation on the substrate and the ring gasket of the holder; and "3" having liquid accumulation on the substrate, seal and bottom metal lip of the holder.

3. The average of all evaluations over time for all replicates is used to determine the average sweat rating of a test membrane.

C. Apparatus/Air Freshener Performance Test Methods

C1. Air Freshener on Vent Vapor Release Rate Test Method (AF on Vent Test Method)

The vapor release rate of Air freshener Samples are evaluated according to the following steps:

1. Measure the initial total sample weight.

2. Clip the sample on a desktop fan such that a coated side (2C on 2B) of the test membrane faces the fan with the fan operating at an air velocity of 3 to 6 m/s (approximately average air velocity of 5 m/s) for 2 hours to simulate an on-vent state when the fan of an air conditioning system is turned on. The desktop fan is selected to simulate the fan of an air condition system such as for example in an automobile.

3. The fan with the sample clipped thereon is placed in a 2.0 m×3.4 m×2.8 m room. The conditions of the room are:
Air velocity—10 air changes per hour (ACH), velocity~0.1 m/s,
Air Temperature—21 deg C.
Relative Humidity—40% RH.

4. Remove the sample from the fan and measure sample weight corresponding to an on-vent condition "ON" state in which the fan is turned on.

5. Place the sample in a room at 21 deg C., 60% RH and 10ACH for 22 hours (to simulate an off vent condition in which the fan is not turned on).

6. Remove the sample from the room and measure sample weight so as to obtain a sample weight corresponding to an off-vent condition, i.e. when the apparatus is not placed on the vent ("OFF" state).

7. Repeat Steps 4 to 6 above on a daily basis.

8. Measure change in sample weight and calculate perfume evaporation rates over 30 days.

9. Determine the cumulative weight loss of the volatile composition as described thereinafter using the recorded times with their corresponding weights.

10. Calculate the time average vapor release rate of the volatile composition as described hereinafter using the recorded times and their corresponding weights.

C2. Cumulative Weight Loss Calculation Method

A cumulative weight loss at a time after activation is calculated following formula (1)

$$\text{Cumulative Weight Loss at } T_x = W\text{cum}T_x = W_{Ti} - W_{Tx} \quad (1)$$

wherein
$W_{Ti}$=initial weight of volatile composition (mg) prior to activation
$W_{Tx}$=weight of volatile composition (mg) at a designated time (days) after activation C3. Average Vapor Release Rate Calculation Method An average vapor release rate of the air freshener is calculated using formula (2).

Time average vapor release rate, $$V = \frac{W_1 - W_2}{(t_2 - t_1)} \quad (2)$$

wherein,
$t_1$=a first time period after activation
$t_2$=a second time period after activation
$W_1$=weight of the volatile composition at $t_1$
$W_2$=weight of the volatile composition at $t_2$.

Example I

Figure 8:
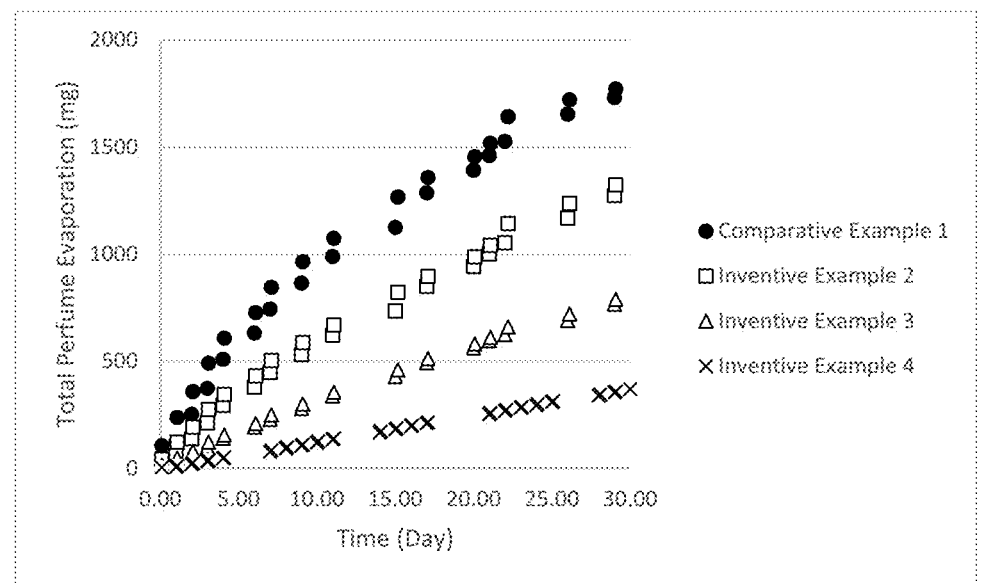
FIG. 8 is a graph showing the cumulative amount of a volatile composition of a volatile composition contained in Comparative Example 1 and Inventive Examples 2, 3 and 4 released over time.
Figure 9:
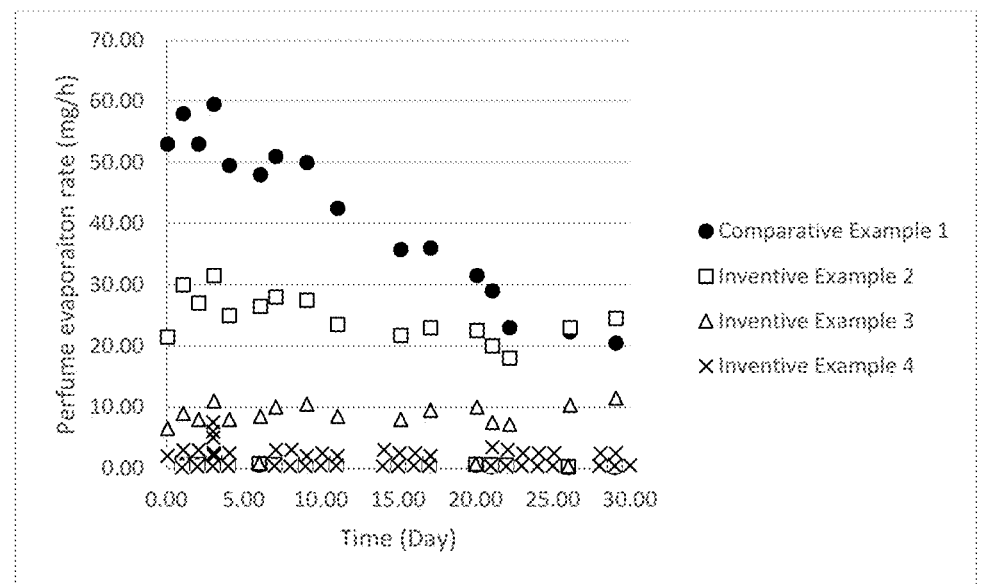
FIG. 9 is a graph showing a vapor release rate/perfume evaporation rate in milligrams per hour of a volatile composition contained in Comparative Example 1 and Inventive Examples 2, 3 and 4 released over time.

In this example, inventive air fresheners based on the apparatus of FIG. 5 and the volatile composition of Table 3 ("Inventive Examples 2, 3, and 4") and comparative air freshener based on the apparatus of FIG. 5 and the volatile composition of Table 3 ("Comparative Example 1") are evaluated according to the Vapor Release Rate Test Method described hereinbefore under Test Methods. Tables 5, 6 and 7 below show a cumulative weight loss and vapor release rate of volatile composition from inventive air fresheners 2, 3, 4 and comparative air freshener 1. FIG. 8 and FIG. 9 are corresponding graphs of Tables 5, 6 and 7.

TABLE 5

| | | Comparative Example (Ex.) 1 | | | Inventive Example (Ex.) 2 | | |
|---|---|---|---|---|---|---|---|
| Day | On Vent ("ON") Off Vent ("OFF") | Cumulative perfume evaporation (mg) | Perfume evaporation rate (mg/h) | Area normalized perfume evaporation rate (mg/h*cm$^2$) | Cumulative perfume evaporation (mg) | Perfume evaporation rate (mg/h) | Area normalized perfume evaporation rate (mg/h*cm$^2$) |
| 0 | OFF | 0 | 0 | 0.00 | 0 | 0 | 0.00 |
| 0.08 | ON | 106 | 53.00 | 7.57 | 43 | 21.50 | 3.07 |
| 1.00 | OFF | 121 | 0.68 | 0.10 | 62 | 0.86 | 0.12 |
| 1.08 | ON | 237 | 58.00 | 8.29 | 122 | 30.00 | 4.29 |

TABLE 5-continued

|  |  | Comparative Example (Ex.) 1 | | | Inventive Example (Ex.) 2 | | |
|---|---|---|---|---|---|---|---|
| Day | On Vent ("ON")/ Off Vent ("OFF") | Cumulative perfume evaporation (mg) | Perfume evaporation rate (mg/h) | Area normalized perfume evaporation rate (mg/h*cm$^2$) | Cumulative perfume evaporation (mg) | Perfume evaporation rate (mg/h) | Area normalized perfume evaporation rate (mg/h*cm$^2$) |
| 2.00 | OFF | 252 | 0.68 | 0.10 | 139 | 0.77 | 0.11 |
| 2.08 | ON | 358 | 53.00 | 7.57 | 193 | 27.00 | 3.86 |
| 3.00 | OFF | 373 | 0.68 | 0.10 | 212 | 0.86 | 0.12 |
| 3.08 | ON | 492 | 59.50 | 8.50 | 275 | 31.50 | 4.50 |
| 4.00 | OFF | 509 | 0.77 | 0.11 | 295 | 0.91 | 0.13 |
| 4.08 | ON | 608 | 49.50 | 7.07 | 345 | 25.00 | 3.57 |
| 6.00 | OFF | 632 | 0.52 | 0.07 | 379 | 0.74 | 0.11 |
| 6.08 | ON | 728 | 48.00 | 6.86 | 432 | 26.50 | 3.79 |
| 7.00 | OFF | 744 | 0.73 | 0.10 | 448 | 0.73 | 0.10 |
| 7.08 | ON | 846 | 51.00 | 7.29 | 504 | 28.00 | 4.00 |
| 9.00 | OFF | 865 | 0.41 | 0.06 | 532 | 0.61 | 0.09 |
| 9.08 | ON | 965 | 50.00 | 7.14 | 587 | 27.50 | 3.93 |
| 11.00 | OFF | 989 | 0.52 | 0.07 | 622 | 0.76 | 0.11 |
| 11.08 | ON | 1074 | 42.50 | 6.07 | 669 | 23.50 | 3.36 |
| 15.00 | OFF | 1125 | 0.54 | 0.08 | 735 | 0.70 | 0.10 |
| 15.17 | ON | 1268 | 35.75 | 5.11 | 822 | 21.75 | 3.11 |
| 17.00 | OFF | 1287 | 0.43 | 0.06 | 850 | 0.64 | 0.09 |
| 17.08 | ON | 1359 | 36.00 | 5.14 | 896 | 23.00 | 3.29 |
| 20.00 | OFF | 1393 | 0.49 | 0.07 | 943 | 0.67 | 0.10 |
| 20.08 | ON | 1456 | 31.50 | 4.50 | 988 | 22.50 | 3.21 |
| 21.00 | OFF | 1461 | 0.23 | 0.03 | 1001 | 0.59 | 0.08 |
| 21.08 | ON | 1519 | 29.00 | 4.14 | 1041 | 20.00 | 2.86 |
| 22.00 | OFF | 1528 | 0.41 | 0.06 | 1053 | 0.55 | 0.08 |
| 22.21 | ON | 1643 | 23.00 | 3.29 | 1143 | 18.00 | 2.57 |
| 26.00 | OFF | 1654 | 0.12 | 0.02 | 1169 | 0.29 | 0.04 |
| 26.13 | ON | 1721 | 22.33 | 3.19 | 1238 | 23.00 | 3.29 |
| 29.00 | OFF | 1732 | 0.16 | 0.02 | 1275 | 0.54 | 0.08 |
| 29.08 | ON | 1773 | 20.50 | 2.93 | 1324 | 24.50 | 3.50 |

TABLE 6

| | | Inventive Example (Ex.) 3 | | |
|---|---|---|---|---|
| Day | On Vent ("ON")/ Off Vent ("OFF") | Cumulative Perfume evaporation (mg) | Perfume evaporation rate (mg/h) | Area normalized perfume evaporation rate (mg/h*cm$^2$) |
| 0 | OFF | 0 | 0 | 0.00 |
| 0.08 | ON | 13 | 6.50 | 0.93 |
| 1.00 | OFF | 30 | 0.77 | 0.11 |
| 1.08 | ON | 48 | 9.00 | 1.29 |
| 2.00 | OFF | 65 | 0.77 | 0.11 |
| 2.08 | ON | 81 | 8.00 | 1.14 |
| 3.00 | OFF | 100 | 0.86 | 0.12 |
| 3.08 | ON | 122 | 11.00 | 1.57 |
| 4.00 | OFF | 140 | 0.82 | 0.12 |
| 4.08 | ON | 156 | 8.00 | 1.14 |
| 6.00 | OFF | 193 | 0.80 | 0.11 |
| 6.08 | ON | 210 | 8.50 | 1.21 |
| 7.00 | OFF | 229 | 0.86 | 0.12 |
| 7.08 | ON | 249 | 10.00 | 1.43 |
| 9.00 | OFF | 279 | 0.65 | 0.09 |
| 9.08 | ON | 300 | 10.50 | 1.50 |
| 11.00 | OFF | 338 | 0.83 | 0.12 |
| 11.08 | ON | 355 | 8.50 | 1.21 |
| 15.00 | OFF | 429 | 0.79 | 0.11 |
| 15.17 | ON | 461 | 8.00 | 1.14 |
| 17.00 | OFF | 493 | 0.73 | 0.10 |
| 17.08 | ON | 512 | 9.50 | 1.36 |
| 20.00 | OFF | 562 | 0.71 | 0.10 |
| 20.08 | ON | 582 | 10.00 | 1.43 |
| 21.00 | OFF | 596 | 0.64 | 0.09 |
| 21.08 | ON | 611 | 7.50 | 1.07 |
| 22.00 | OFF | 625 | 0.64 | 0.09 |
| 22.21 | ON | 661 | 7.20 | 1.03 |

TABLE 6-continued

| | | Inventive Example (Ex.) 3 | | |
|---|---|---|---|---|
| Day | On Vent ("ON")/ Off Vent ("OFF") | Cumulative Perfume evaporation (mg) | Perfume evaporation rate (mg/h) | Area normalized perfume evaporation rate (mg/h*cm$^2$) |
| 26.00 | OFF | 690 | 0.32 | 0.05 |
| 26.13 | ON | 721 | 10.33 | 1.48 |
| 29.00 | OFF | 766 | 0.65 | 0.09 |
| 29.08 | ON | 789 | 11.50 | 1.64 |

TABLE 7

| | | Inventive Example (Ex.) 4 | | |
|---|---|---|---|---|
| Day | On Vent ("ON")/ Off Vent ("OFF") | Cumulative perfume evaporation (mg) | Perfume evaporation rate (mg/h) | Area normalized perfume evaporation rate (mg/h*cm$^2$) |
| 0 | OFF | 0 | 0 | 0 |
| 0.08 | ON | 4 | 2.00 | 0.29 |
| 1.00 | OFF | 6 | 0.09 | 0.01 |
| 1.08 | ON | 12 | 3.00 | 0.43 |
| 2.00 | OFF | 19 | 0.32 | 0.05 |
| 2.08 | ON | 25 | 3.00 | 0.43 |
| 3.00 | OFF | 33 | 0.36 | 0.05 |
| 3.09 | ON | 38 | 2.00 | 0.29 |
| 4.00 | OFF | 46 | 0.37 | 0.05 |
| 4.08 | ON | 51 | 2.50 | 0.36 |

TABLE 7-continued

Inventive Example (Ex.) 4

| Day | On Vent ("ON")/ Off Vent ("OFF") | Cumulative perfume evaporation (mg) | Perfume evaporation rate (mg/h) | Area normalized perfume evaporation rate (mg/h*cm$^2$) |
|---|---|---|---|---|
| 7.00 | OFF | 78 | 0.39 | 0.06 |
| 7.08 | ON | 84 | 3.00 | 0.43 |
| 8.00 | OFF | 92 | 0.36 | 0.05 |
| 8.08 | ON | 98 | 3.00 | 0.43 |
| 9.00 | OFF | 106 | 0.36 | 0.05 |
| 9.08 | ON | 110 | 2.00 | 0.29 |
| 10.00 | OFF | 120 | 0.45 | 0.06 |

TABLE 7-continued

Inventive Example (Ex.) 4

| Day | On Vent ("ON")/ Off Vent ("OFF") | Cumulative perfume evaporation (mg) | Perfume evaporation rate (mg/h) | Area normalized perfume evaporation rate (mg/h*cm$^2$) |
|---|---|---|---|---|
| 10.08 | ON | 125 | 2.50 | 0.36 |
| 11.00 | OFF | 135 | 0.45 | 0.06 |
| 11.08 | ON | 139 | 2.00 | 0.29 |
| 14.00 | OFF | 168 | 0.41 | 0.06 |
| 14.08 | ON | 174 | 3.00 | 0.43 |
| 15.00 | OFF | 182 | 0.36 | 0.05 |
| 15.08 | ON | 187 | 2.50 | 0.36 |
| 16.00 | OFF | 197 | 0.45 | 0.06 |
| 16.08 | ON | 202 | 2.50 | 0.36 |
| 17.00 | OFF | 211 | 0.41 | 0.06 |
| 17.08 | ON | 215 | 2.00 | 0.29 |
| 21.00 | OFF | 252 | 0.39 | 0.06 |
| 21.08 | ON | 259 | 3.50 | 0.50 |
| 22.00 | OFF | 267 | 0.36 | 0.05 |
| 22.08 | ON | 273 | 3.00 | 0.43 |
| 23.00 | OFF | 282 | 0.41 | 0.06 |
| 23.08 | ON | 287 | 2.50 | 0.36 |
| 24.00 | OFF | 295 | 0.36 | 0.05 |
| 24.08 | ON | 300 | 2.50 | 0.36 |
| 25.00 | OFF | 309 | 0.41 | 0.06 |
| 25.08 | ON | 314 | 2.50 | 0.36 |
| 28.00 | OFF | 340 | 0.37 | 0.05 |
| 28.08 | ON | 345 | 2.50 | 0.36 |
| 29.00 | OFF | 354 | 0.41 | 0.06 |
| 29.08 | ON | 359 | 2.50 | 0.36 |
| 30.00 | OFF | 369 | 0.45 | 0.06 |

As described hereinbefore, each of Inventive Examples 2, 3 and 4 comprise a composite membrane comprising a hydrophobic/oleophobic coating 2C and a hydrophilic coating 2B. By having the combination of a volatile composition 9 and a composite membrane 13 having a hydrophobic/oleophobic coating 2C and the hydrophilic coating 2B, the overall cumulative perfume evaporation of each of the Inventive Samples is reduced relative to a cumulative perfume evaporation of the uncoated microporous membrane (Comparative Example 1) as illustrated in FIG. 8.

Referring to Tables 5, 6 and 7, the vapor release rates or perfume evaporation rates of Inventive Examples 2, 3 and 4 are reduced by 58% to 96% relative to a vapor release rate/perfume evaporation rate of Comparative Example 1 (without a composite membrane but using a non-coated membrane) at Day 0.08 when there is high air flow (for example at an average air flow rate of 5 m/s) across the membrane surface (i.e. when the samples were placed on the fan for 2 hours as described in the Vapor Release Rate Test Method). A sample calculation of a percentage reduction of the vapor release rate at Day 0.08 ("ON"/Fan turned on) for Inventive Examples 2, 3 and 4 relative to the Comparative Example 1 are shown below.

| Day 0.08 ("ON") | Comparative Ex. 1 | Inventive Ex. 2 (Composite Membrane 1) | Inventive Ex. 3 (Composite Membrane 2) | Inventive Ex. 4 (Composite Membrane 3) |
|---|---|---|---|---|
| mg/h | 53 | 21.5 | 6.5 | 2 |
| Difference in mg/hr relative to Comparative Ex. 1 | — | 31.5 | 46.5 | 51 |
| % reduction relative to Comparative Ex. 1 | — | 58% | 87% | 96% |
| mg/h*cm2 | 7.57 | 3.07 | 0.93 | 0.29 |

Accordingly, a technical effect of the present invention is it provides overall reduced perfume evaporation rates when the apparatus according to the present invention is subject to high air flow conditions such as placed in a car when the car is moving or when placed on vent in fluid communication with a fan of the air conditioning system ("ON"—there is high air flow) thereby corresponds to reduced scent intensity in the interior space when the fan of the air conditioning system is turned on.

Example II

Figure 10:
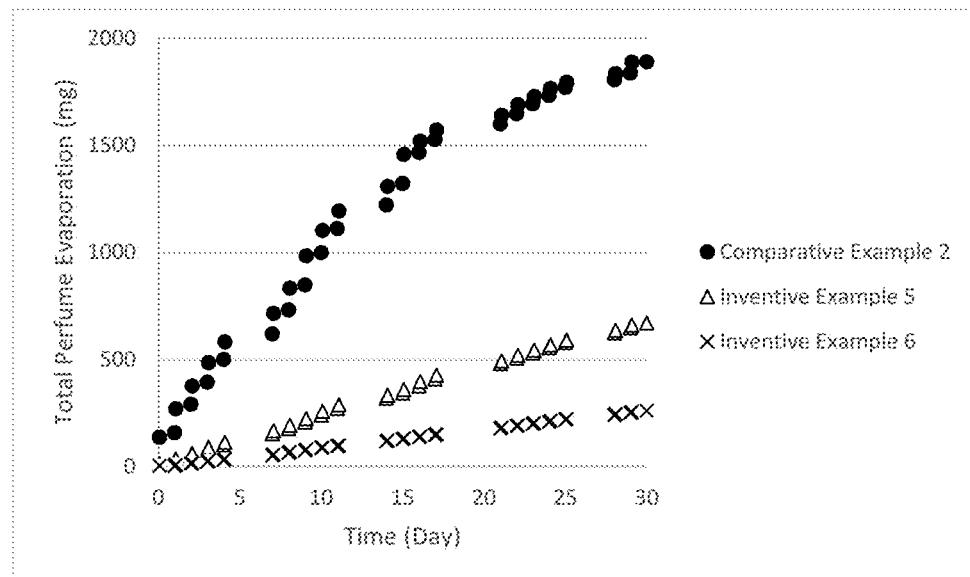
FIG. 10 is a graph showing the cumulative amount of a volatile composition contained in Comparative Example 2 and Inventive Examples 5 and 6 released over time.
Figure 11:
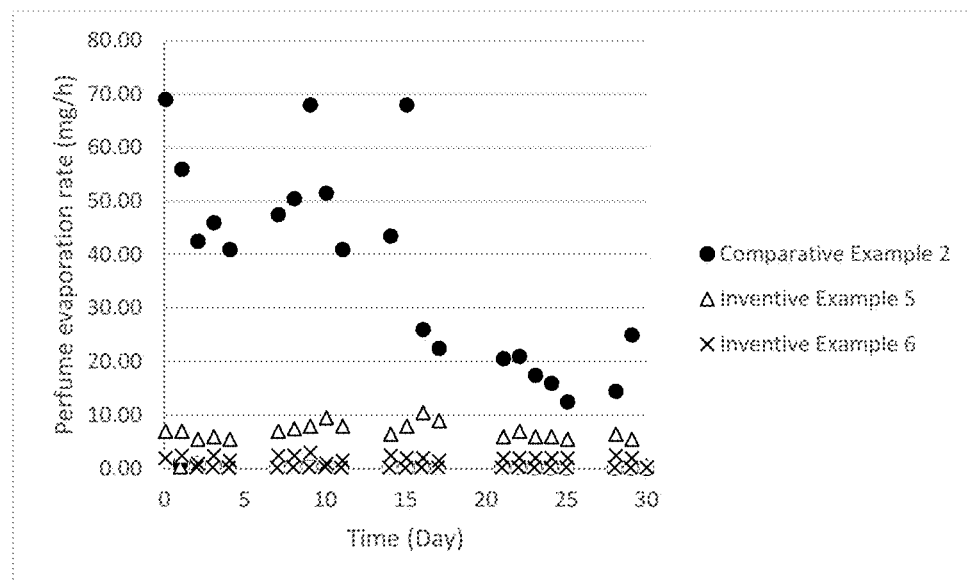
FIG. 11 is a graph showing a vapor release rate/perfume evaporation rate in milligrams per hour of a volatile composition contained in Comparative Example 2 and Inventive Examples 5 and 6 released over time.

Inventive Examples 5 and 6 and Comparative Example 2 are evaluated according to the Vapor Release Rate Test Method described hereinbefore under Test Methods. Table 8 below show a cumulative weight loss, vapor release rate, and of volatile composition from Comparative Example 2. Table 9 below show a cumulative weight loss, vapor release rate, and of volatile composition from Inventive Examples 5, 6. FIG. 10 and FIG. 11 are corresponding graphs of Tables 8 and 9.

TABLE 8

Comparative Example 2

| Day | On Vent ("ON")/ Off Vent ("OFF") | Cumulative perfume evaporation (mg) | Perfume evaporation rate (mg/h) | Area normalized perfume evaporation rate (mg/h*cm$^2$) |
|---|---|---|---|---|
| 0 | OFF | 0 | 0 | 0 |
| 0.08 | ON | 138 | 69.00 | 9.86 |
| 1.00 | OFF | 158 | 0.91 | 0.13 |
| 1.08 | ON | 270 | 56.00 | 8.00 |
| 2.00 | OFF | 291 | 0.95 | 0.14 |
| 2.08 | ON | 376 | 42.50 | 6.07 |
| 3.00 | OFF | 394 | 0.82 | 0.12 |

TABLE 8-continued

Comparative Example 2

| Day | On Vent ("ON")/ Off Vent ("OFF") | Cumulative perfume evaporation (mg) | Perfume evaporation rate (mg/h) | Area normalized perfume evaporation rate (mg/h*cm$^2$) |
| --- | --- | --- | --- | --- |
| 3.08 | ON | 486 | 46.00 | 6.57 |
| 4.00 | OFF | 500 | 0.64 | 0.09 |
| 4.08 | ON | 582 | 41.00 | 5.86 |
| 7.00 | OFF | 620 | 0.54 | 0.08 |
| 7.08 | ON | 715 | 47.50 | 6.79 |
| 8.00 | OFF | 732 | 0.77 | 0.11 |
| 8.08 | ON | 833 | 50.50 | 7.21 |
| 9.00 | OFF | 849 | 0.73 | 0.10 |
| 9.08 | ON | 985 | 68.00 | 9.71 |
| 10.00 | OFF | 1000 | 0.68 | 0.10 |
| 10.08 | ON | 1103 | 51.50 | 7.36 |
| 11.00 | OFF | 1112 | 0.41 | 0.06 |
| 11.08 | ON | 1194 | 41.00 | 5.86 |
| 14.00 | OFF | 1222 | 0.40 | 0.06 |
| 14.08 | ON | 1309 | 43.50 | 6.21 |
| 15.00 | OFF | 1323 | 0.64 | 0.09 |
| 15.08 | ON | 1459 | 68.00 | 9.71 |
| 16.00 | OFF | 1468 | 0.41 | 0.06 |
| 16.08 | ON | 1520 | 26.00 | 3.71 |
| 17.00 | OFF | 1527 | 0.32 | 0.05 |
| 17.08 | ON | 1572 | 22.50 | 3.21 |
| 21.00 | OFF | 1599.8 | 0.30 | 0.04 |
| 21.08 | ON | 1641 | 20.60 | 2.94 |
| 22.00 | OFF | 1648 | 0.32 | 0.05 |
| 22.08 | ON | 1690 | 21.00 | 3.00 |
| 23.00 | OFF | 1694 | 0.18 | 0.03 |
| 23.08 | ON | 1729 | 17.50 | 2.50 |
| 24.00 | OFF | 1734 | 0.23 | 0.03 |
| 24.08 | ON | 1766 | 16.00 | 2.29 |
| 25.00 | OFF | 1770 | 0.18 | 0.03 |
| 25.08 | ON | 1795 | 12.50 | 1.79 |
| 28.00 | OFF | 1806 | 0.16 | 0.02 |
| 28.08 | ON | 1835 | 14.50 | 2.07 |
| 29.00 | OFF | 1838 | 0.14 | 0.02 |
| 29.08 | ON | 1888 | 25.00 | 3.57 |
| 30.00 | OFF | 1890 | 0.09 | 0.01 |

TABLE 9

| | | Inventive Example 5 | | | Inventive Example 6 | | |
| --- | --- | --- | --- | --- | --- | --- | --- |
| Day | On Vent ("ON")/ Off Vent ("OFF") | Cumulative perfume evaporation (mg) | Perfume evaporation rate (mg/h) | Area normalized perfume evaporation rate (mg/h*cm$^2$) | Cumulative Perfume evaporation (mg) | Perfume evaporation rate (mg/h) | Area normalized perfume evaporation rate (mg/h*cm$^2$) |
| 0 | OFF | 0 | 0 | 0 | 0 | 0 | 0 |
| 0.08 | ON | 14 | 7.00 | 1.00 | 4 | 2.00 | 0.29 |
| 1.00 | OFF | 22 | 0.36 | 0.05 | 3 | 0 | 0.00 |
| 1.08 | ON | 36 | 7.00 | 1.00 | 8 | 2.50 | 0.36 |
| 2.00 | OFF | 50 | 0.64 | 0.09 | 14 | 0.27 | 0.04 |
| 2.08 | ON | 61 | 5.50 | 0.79 | 16 | 1.00 | 0.14 |
| 3.00 | OFF | 77 | 0.73 | 0.10 | 22 | 0.27 | 0.04 |
| 3.08 | ON | 89 | 6.00 | 0.86 | 27 | 2.50 | 0.36 |
| 4.00 | OFF | 102 | 0.59 | 0.08 | 31 | 0.18 | 0.03 |
| 4.08 | ON | 113 | 5.50 | 0.79 | 34 | 1.50 | 0.21 |
| 7.00 | OFF | 153 | 0.57 | 0.08 | 52 | 0.26 | 0.04 |
| 7.08 | ON | 167 | 7.00 | 1.00 | 57 | 2.50 | 0.36 |
| 8.00 | OFF | 178 | 0.50 | 0.07 | 64 | 0.32 | 0.05 |
| 8.08 | ON | 193 | 7.50 | 1.07 | 69 | 2.50 | 0.36 |
| 9.00 | OFF | 208 | 0.68 | 0.10 | 75 | 0.27 | 0.04 |
| 9.08 | ON | 224 | 8.00 | 1.14 | 81 | 3.00 | 0.43 |
| 10.00 | OFF | 240 | 0.73 | 0.10 | 88 | 0.32 | 0.05 |
| 10.08 | ON | 259 | 9.50 | 1.36 | 90 | 1.00 | 0.14 |
| 11.00 | OFF | 272 | 0.59 | 0.08 | 95 | 0.23 | 0.03 |
| 11.08 | ON | 288 | 8.00 | 1.14 | 98 | 1.50 | 0.21 |
| 14.00 | OFF | 320 | 0.46 | 0.07 | 118 | 0.29 | 0.04 |
| 14.08 | ON | 333 | 6.50 | 0.93 | 123 | 2.50 | 0.36 |
| 15.00 | OFF | 344 | 0.50 | 0.07 | 128 | 0.23 | 0.03 |
| 15.08 | ON | 360 | 8.00 | 1.14 | 132 | 2.00 | 0.29 |
| 16.00 | OFF | 376 | 0.73 | 0.10 | 138 | 0.27 | 0.04 |
| 16.08 | ON | 397 | 10.50 | 1.50 | 142 | 2.00 | 0.29 |
| 17.00 | OFF | 409 | 0.55 | 0.08 | 148 | 0.27 | 0.04 |
| 17.08 | ON | 427 | 9.00 | 1.29 | 151 | 1.50 | 0.21 |
| 21.00 | OFF | 481 | 0.57 | 0.08 | 178 | 0.29 | 0.04 |
| 21.08 | ON | 493 | 6.00 | 0.86 | 182 | 2.00 | 0.29 |
| 22.00 | OFF | 506 | 0.59 | 0.08 | 189 | 0.32 | 0.05 |
| 22.08 | ON | 520 | 7.00 | 1.00 | 193 | 2.00 | 0.29 |
| 23.00 | OFF | 531 | 0.50 | 0.07 | 199 | 0.27 | 0.04 |
| 23.08 | ON | 543 | 6.00 | 0.86 | 203 | 2.00 | 0.29 |

TABLE 9-continued

|  |  | Inventive Example 5 | | | Inventive Example 6 | | |
| --- | --- | --- | --- | --- | --- | --- | --- |
| Day | On Vent ("ON")/ Off Vent ("OFF") | Cumulative perfume evaporation (mg) | Perfume evaporation rate (mg/h) | Area normalized perfume evaporation rate (mg/h*cm$^2$) | Cumulative Perfume evaporation (mg) | Perfume evaporation rate (mg/h) | Area normalized perfume evaporation rate (mg/h*cm$^2$) |
| 24.00 | OFF | 555 | 0.55 | 0.08 | 209 | 0.27 | 0.04 |
| 24.08 | ON | 567 | 6.00 | 0.86 | 213 | 2.00 | 0.29 |
| 25.00 | OFF | 579 | 0.55 | 0.08 | 219 | 0.27 | 0.04 |
| 25.08 | ON | 590 | 5.50 | 0.79 | 223 | 2.00 | 0.29 |
| 28.00 | OFF | 624 | 0.49 | 0.07 | 240 | 0.24 | 0.03 |
| 28.08 | ON | 637 | 6.50 | 0.93 | 245 | 2.50 | 0.36 |
| 29.00 | OFF | 649 | 0.55 | 0.08 | 251 | 0.27 | 0.04 |
| 29.08 | ON | 660 | 5.50 | 0.79 | 255 | 2.00 | 0.29 |
| 30.00 | OFF | 671 | 0.50 | 0.07 | 261 | 0.27 | 0.04 |

Inventive Examples 5 and 6 use composite membranes comprising a hydrophilic material and a hydrophobic and oleophobic material to define the diffusion regulating coating. A sample calculation of a percentage reduction of the vapor release rate at Day 0.08 ("ON"/Fan turned on) for Inventive Examples 5 and 6 relative to the Comparative Example 2 are shown below.

| Day 0.08 ("ON") | Comparative Ex. 2 | Inventive Ex. 5 (Composite Membrane 2) | Inventive Ex. 6 (Composite Membrane 3) |
| --- | --- | --- | --- |
| mg/h | 69 | 7 | 2 |
| Reduction mg/h relative to Comparative Ex 2 | — | 62 | 67 |
| % reduction relative to Comparative Ex 2 | — | 89% | 97% |
| mg/h*cm2 | 9.86 | 1.00 | 0.29 |

Accordingly, a technical effect of the present invention is it provides overall reduced perfume evaporation rates (vapor release rates) when the apparatus according to the present invention is subject to high air flow conditions such as for example when the car is moving or when placed on vent in fluid communication with a fan of the air conditioning system ("ON"—there is high air flow) thereby corresponds to reduced scent intensity in the interior space when the fan of the air conditioning system is turned on.

Example III

Physical and/or performance characteristics of a membrane (such as a composite membrane) based on a desired vapor release rate of the apparatus 1 (such as for example a vapor release rate in the range of equal to or greater than 0.2 mg/hr*cm$^2$ to 5 mg/hr*cm$^2$ at an average air flow rate of 5 m/s) may be determined by the Gurley Porosity, Density, Pore Size, Contact Angle, Oil Rating, Volatile Material Transfer Rate, and Sweat Rating Test Methods respectively described hereinbefore.

Table 10 shows different combinations of a composite membrane having different treatments that define one or more diffusion regulating coatings for the composite membrane in an apparatus according to the present invention. Table 11 shows the compositions of filled microporous membranes before coating (substrate). Table 11 shows vapor material transfer rates of each of the composite membranes of Table 10.

TABLE 10

| Composite Membrane Example | Substrate Example | Side A (first side 134 of FIG. 2) | Side B (second side 136 of FIG. 2) | Porosity, Gurley (sec) | Density (g/cm3) | Mean pore size (microns) | Contact Angle (Side A) | Oil Rating (Side A) |
| --- | --- | --- | --- | --- | --- | --- | --- | --- |
| 4 | 3 | 2C | — | 8477 | 0.9 | 0.03 | 107 | 7 |
| 5 | 1 | 2A/2C | 2A | 1297 | 0.57 | 0.05 | 118 | 7 |
| 6 | 3 | 2A/2C | 2A | 8477 | 0.9 | 0.03 | 107 | 7 |
| 7 | 3 | 2A/2C | 2A/2C | 3096 | 0.74 | 0.04 | 115 | 7 |
| CE-8 | 1 | — | — | 1297 | 0.55 | 0.05 | 114 | 2 |
| CE-9 | 2 | — | — | 5959 | 0.66 | 0.04 | 116 | 2 |
| CE-10 | 3 | — | — | 8477 | 0.74 | 0.03 | 105 | 2 |
| CE-11 | 2 | 2A | 2A | 5959 | 0.66 | 0.05 | <20 | 2 |
| CE-12 | 1 | 2A/2B | 2A | 1297 | 0.56 | 0.05 | 51 | 3 |
| CE-13 | DURAPEL ® GVSP[1] | — | — | 150 | 0.67 | 0.44[2] | 153 | 6 |

TABLE 11

| Ingredients (wt. %) | Substrate Example 1 | Substrate Example 2 | Substrate Example 3 |
|---|---|---|---|
| GUR ® 4170[3] | 9.08 | — | — |
| GUR ® 4130[4] | — | 9.16 | 9.60 |
| FINA ® 1288[5] | — | 9.16 | 8.75 |
| HI-SIL ® 135[6] | 31.77 | 30.89 | 24.86 |
| TIPURE ® R-103[7] | 1.40 | 1.28 | 1.71 |
| CaCO3 | — | — | 10.03 |
| Calcium stearate | 0.41 | 0.26 | 0.27 |
| CYANOX ® 1790[8] | 0.33 | 0.26 | 0.18 |
| TUFFLO ® 6056[9] | 57.01 | 49.00 | 44.59 |

TABLE 12

| Composite Membrane Example | Volatile Material Transfer Rate (mg/(hr*cm$^2$)) | | | | Sweat Rating | |
|---|---|---|---|---|---|---|
| | Full Non-restricted | Full Restricted | Quarter Charge Non-restricted | Quarter Charge Restricted | Full Non-restricted | Full restricted |
| 4 | 0.33 | 0.06 | 0.27 | 0.05 | 0 | 0 |
| 5A | 0.28 | 0.04 | 0.18 | 0.04 | 0 | 0 |
| 5B (Side B is exposed to reservoir) | 0.29 | 0.05 | 0.20 | 0.03 | 0 | 0 |
| 6 | 0.33 | 0.05 | 0.27 | 0.05 | 0 | 0 |
| 7 | 0.18 | 0.06 | 0.25 | 0.03 | 0 | 0 |
| CE-8 | 0.3 | 0.12 | 0.17 | 0.04 | 2.15 | 2.4 |
| CE-9 | 0.31 | 0.03 | 0.19 | 0.04 | 0 | 0.8 |
| CE-10 | 0.29 | 0.04 | 0.3 | 0.04 | 0 | 0.47 |
| CE-11 | 0.38 | 0.07 | 0.3 | 0.06 | 0 | 0.3 |
| CE-12 | 0.25 | 0.04 | 0.17 | 0.03 | 0.14 | 0.25 |
| CE-13 | 0.1 | <<0.01[10] | 0.1 | <<0.01 | 0 | N/A |

Results in Table 12 show that providing a composite membrane with a hydrophilic coating 2A and a hydrophobic/oleophobic coating 2C (Example 7) provides a reduction in the vapor release rate of the composite membrane (0.18 mg/hr*cm2) by approximately 60% relative to an uncoated membrane (CE-10) having a vapor release rate of 0.29 mg/hr*cm2.

[1] A PVDF porous membrane with a superhydrophobic surface, available from MilliporeSigma (Billerica, Mass.).
[2] Durapel GVSP has a reported mean pore size of 0.22 micron. Data in Table 9 is as measured according to the Test Methods described hereinbefore.
[3] An Ultra High Molecular Weight Polyethylene (UHMWPE), available from Celanese Corporation (Irving, Tex.)
[4] An Ultra High Molecular Weight Polyethylene (UHMWPE), available from Celanese Corporation (Irving, Tex.)
[5] High Density Polyethylene (HDPE), available from Total Petrochemicals USA Inc. (Houston, Tex.)
[6] Precipitated silica available from PPG Industries, Inc. (Pittsburgh, Pa.)
[7] Rutile titanium dioxide available from The Chemours Company (Wilmington, Del.)
[8] A phenolic antioxidant available from Cytec Solvay Group (Woodland Park, N.J.)
[9] A process oil available from PPC Lubricants (Jonestown, Pa.)
[10] Over a 14 day period, no measurable change in weight was observed under restricted conditions, indicating that the membrane was not operating as a vapor permeable membrane. Thus, a sweat rating was not relevant.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus (1) for air freshening in an interior occupancy space, the apparatus (1) comprising:
   a) a reservoir (11) containing a volatile composition (9) for air freshening and/or malodor removal;
   b) a composite membrane (13) in fluid communication with the volatile composition (9); wherein the composite membrane (13) comprises a first side (134) facing the reservoir (11) and a second side (136) opposite the first side (134);
   c) wherein at least one of the first side (134) and the second side (136) comprises a diffusion regulating coating (138), wherein the diffusion regulating coating (138) comprises a hydrophobic/oleophobic material (2C) comprising at least one fluoro-alkyl group;
   d) wherein the volatile composition (9) comprises at least 20% of perfume raw materials by weight of the composition (9), wherein the at least 20% of perfume raw materials have an average vapor pressure equal to or greater than 0.01 torr at 25 degrees Celsius;
   e) wherein the apparatus (1) comprises an average vapor release rate from 0.2 mg/hr*cm$^2$ to 5 mg/hr*cm$^2$ at an air flow rate of 5 m/s+/−1 m/s and a temperature of 21 degrees Celsius.

2. The apparatus (1) according to claim 1, wherein the hydrophobic/oleophobic material (2C) is over at least a portion of the second side (136).

3. The apparatus (1) according to claim 1, wherein the hydrophobic/oleophobic material (2C) comprises a fluoro-alkyl group containing co-polymer.

4. The apparatus (1) according to claim 1, wherein the hydrophobic/oleophobic material (2C) comprises one or more of a fluoroalkyl acrylate copolymer, perfluoroalkoxy polymer, polytetrafluoroethylene, fluorinated ethylene-propylene, polyethylenetetrafluoroethylene, perfluoro elastomers, perfluoropolyether, fluorosilicones, fluorosilanes, perfluorosilane and fluoroalkylsilsequioxane.

5. The apparatus (1) according to claim 1, wherein the diffusion regulating coating (138) further comprises a polymer material (2), wherein the polymer material (2) is a hydrophilic material (2B) or a hydrophobic material, preferably a hydrophilic material (2B).

6. The apparatus (1) according to claim 5, wherein the polymer material (2) is over at least a portion of the at least one of the first side (134) and the second side (136), preferably at least a portion of the second side (136).

7. The apparatus (1) according to claim 6, wherein the hydrophobic/oleophobic material (2C) is on the polymer material (2).

8. The apparatus (1) according to claim 5, wherein the polymer material (2) is a hydrophobic material, preferably the hydrophobic material comprises one or more of a polysiloxane, polydimethylsiloxane, polyvinylidene fluoride, polyacrylonitrile and combinations thereof.

9. The apparatus (1) according to claim 5, wherein the polymer material (2) is a hydrophilic material (2B), preferably the hydrophilic material (2B) comprises one or more of a polyoxazoline, triblock copolymers based on poly(ethylene glycol)-poly(propylene glycol)-poly(ethylene glycol), polyamide, oxidized polyethylene or its derivatives, polyethyleneoxide, polyvinylpyrrolidone, poly(meth)acrylic acid, polyethylene glycol or its derivatives, polypropylene oxide or its derivatives, a copolymer of poly(ethylene glycol) and polyethyleneoxide, polyvinyl alcohol, cellulose or its derivatives, collagen, polypeptides, guar, pectin, polyimide, poly(meth)acrylamide, polysaccharides, zwitterionic polymers, polyampholytes, polyethylenimine and combinations thereof, preferably the hydrophilic material (2B) comprises polyvinyl alcohol.

10. The apparatus (1) according to claim 1, wherein the volatile composition (9) is in an amount of 1 ml to 50 ml, preferably 2 ml to 40 ml, more preferably 2 ml to 30 ml, even more preferably 2 ml to 3 ml.

11. The apparatus (1) according to claim 1, wherein the average vapor release rate of the apparatus (1) is 1.5 mg/hr*cm$^2$ to 3 mg/hr*cm$^2$, preferably 1.5 mg/hr*cm$^2$ at an air flow rate of 0.5 to 5 m/s and a temperature of 21 degrees Celsius over a time period of 1 to 60 days, preferably 1 to 45 days, more preferably 1 to 30 days.

12. The apparatus (1) according to claim 1, wherein the composite membrane (13) comprises an evaporative surface area from 2 cm$^2$ to 80 cm$^2$, preferably from 2 cm$^2$ to 54 cm$^2$, more preferably from 5 cm$^2$ to 27 cm$^2$, even more preferably from 5 cm$^2$ to 10 cm$^2$, yet even more preferably 5 cm$^2$ to 7 cm$^2$.

13. The apparatus (1) of claim 1, further comprising a vapor impermeable substrate (14) arranged within the apparatus (1) to prevent release of the volatile composition (9) before activation.

14. The apparatus (1) of claim 13, wherein the vapor impermeable substrate (14) is adjacent to the second side (136) and removably attached to a periphery of the reservoir (11) to form a sealed reservoir.

15. The apparatus (1) of claim 13, wherein the vapor impermeable substrate (14) is rupturable, preferably the apparatus (1) is operably connected to an actuator (23) configured for rupturing the vapor impermeable substrate (14), preferably the actuator (23) is a mounting portion for releasably attaching the apparatus (1) to an air vent (33) in the interior occupancy space.

16. A method for air freshening in an interior occupancy space, the method comprising the steps of:
    obtaining an apparatus (1) for air freshening in an interior occupancy space, the apparatus (1) comprising:
    a) a reservoir (11) containing a volatile composition (9) for air freshening and/or malodor removal;
    b) a composite membrane (13) in fluid communication with the volatile composition (9); wherein the composite membrane (13) comprises a first side (134) facing the reservoir (11) and a second side (136) opposite the first side (134);
    c) wherein at least one of the first side (134) and the second side (136) comprises a diffusion regulating coating (138), wherein the diffusion regulating coating (138) comprises a hydrophobic/oleophobic material (2C) comprising at least one fluoro-alkyl group;
    d) wherein the volatile composition (9) comprises at least 20% of perfume raw materials by weight of the composition (9), wherein the at least 20% of perfume raw materials have an average vapor pressure equal to or greater than 0.01 torr at 25 degrees Celsius;
    e) wherein the apparatus (1) comprises an average vapor release rate from 0.2 mg/hr*cm$^2$ to 5 mg/hr*cm$^2$ at an air flow rate of 5 m/s+/−1 m/s and a temperature of 21 degrees Celsius;
    operably connecting the apparatus (1) to a mounting portion; and
    attaching the mounting portion to an air vent.

* * * * *